United States Patent
Shirota et al.

(10) Patent No.: US 9,701,146 B2
(45) Date of Patent: Jul. 11, 2017

(54) INK SET AND THERMAL TRANSFER RECORDING SHEET

(71) Applicant: CANON KABUSHIKI KAISHA, Tokyo (JP)

(72) Inventors: Koromo Shirota, Kawasaki (JP); Taichi Shintou, Saitama (JP); Masao Nakano, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/130,695

(22) Filed: Apr. 15, 2016

(65) Prior Publication Data

US 2016/0303882 A1    Oct. 20, 2016

(30) Foreign Application Priority Data

Apr. 17, 2015  (JP) ................. 2015-085300

(51) Int. Cl.

| | | |
|---|---|---|
| B41M 5/385 | (2006.01) | |
| C07D 417/06 | (2006.01) | |
| C09B 23/00 | (2006.01) | |
| C09D 11/40 | (2014.01) | |
| C09B 23/01 | (2006.01) | |
| C09B 29/036 | (2006.01) | |
| C09B 23/04 | (2006.01) | |
| C09B 1/22 | (2006.01) | |
| C09B 26/02 | (2006.01) | |
| C09B 29/01 | (2006.01) | |
| C09B 25/00 | (2006.01) | |
| C09B 29/08 | (2006.01) | |
| C09B 29/42 | (2006.01) | |
| C09D 11/30 | (2014.01) | |
| C09B 55/00 | (2006.01) | |
| C09B 57/00 | (2006.01) | |
| C09B 1/54 | (2006.01) | |

(52) U.S. Cl.
CPC .......... *B41M 5/3858* (2013.01); *C07D 417/06* (2013.01); *C09B 1/22* (2013.01); *C09B 1/545* (2013.01); *C09B 1/547* (2013.01); *C09B 23/0075* (2013.01); *C09B 23/04* (2013.01); *C09B 25/00* (2013.01); *C09B 26/02* (2013.01); *C09B 29/0007* (2013.01); *C09B 29/0048* (2013.01); *C09B 29/081* (2013.01); *C09B 29/363* (2013.01); *C09B 55/009* (2013.01); *C09B 57/00* (2013.01); *C09D 11/30* (2013.01); *C09D 11/40* (2013.01); *B41M 2205/30* (2013.01)

(58) Field of Classification Search
CPC ...... B41M 5/385–5/39; B41M 2205/30; C09B 23/0075; C07D 417/06
USPC ........................................ 503/227; 106/31.21
See application file for complete search history.

(56) References Cited

FOREIGN PATENT DOCUMENTS

| | | |
|---|---|---|
| JP | 05-262056 A | 10/1993 |
| JP | 07-096675 A | 4/1995 |
| JP | 08-011450 A | 1/1996 |
| JP | 2014-80539 A | 5/2014 |
| WO | 92-19684 A1 | 11/1992 |
| WO | 2008-114886 A1 | 9/2008 |

*Primary Examiner* — Bruce H Hess

(74) *Attorney, Agent, or Firm* — Canon U.S.A., Inc., IP Division

(57) ABSTRACT

An ink set contains a first ink containing a compound in which a pyrazolone ring and a thiazole ring are bonded and a second ink containing a compound in which a pyrazolone ring and a pyridinedione ring are bonded. A thermal transfer recording sheet has a first ink layer containing a compound in which a pyrazolone ring and a thiazole ring are bonded and a second ink layer containing a compound in which a pyrazolone ring and a pyridinedione ring are bonded.

6 Claims, No Drawings

INK SET AND THERMAL TRANSFER RECORDING SHEET

BACKGROUND

Field of the Disclosure

The present disclosure relates to an ink set and a thermal transfer recording sheet.

Description of the Related Art

In recent years, a demand for color-printing in a simple manner photographs/documents taken/created by devices has rapidly further increased with the widespread use of portable color display devices. In particular, in image forming methods employing a thermal transfer technique, the clearness and the color reproduction properties of images are excellent because a dye is used as a coloring agent, a dry process not involving wastewater problems is employed, and the like. Therefore, the demand for the image forming methods has expanded.

As one of the image forming methods employing a thermal transfer technique, a fabric printing method employing a fabric of polyester or the like as a material to be recorded is known. Japanese Patent Laid-Open No. 2014-80539 reports an example of ink jet transfer printing using an anthraquinone-based compound.

However, when an anthraquinone-based magenta pigment and a cyan pigment have been combined, there has been a problem that the reproduction of a red color gamut with a high color saturation demanded in sportswears and the like and a black color with a high density and a high grade has been difficult to achieve.

On the other hand, as one of the image forming methods employing a thermal transfer technique, a thermal transfer recording system employing a thermal transfer sheet is known. As coloring materials for use in the thermal transfer recording system, examples using a yellow dye, a magenta dye, and a cyan dye have been reported (Japanese Patent Laid-Open Nos. 05-262056, 07-096675, and 08-011450). Image formation is performed using ink sheets created using the yellow dye, the magenta dye, and the cyan dye. Therefore, the reproduction of black can be achieved by mixing the three colors (process black). In order to obtain a high grade process black, it is necessary to use a combination of coloring materials having uniform absorption in all the regions of the visible light spectrum. However, when the clearness and the color reproduction properties of an image have been further demanded, a dye with a higher color saturation having a very steep and narrow absorption spectrum has been used, which has posed a problem that wavelength components which cannot be absorbed have remained in color mixing, resulting in the fact that a high grade black has not been able to be formed.

SUMMARY OF THE DISCLOSURE

The present disclosure provides an ink set and a thermal transfer recording sheet having a wide reproducible color gamut in the red region and capable of reproducing a black color with a high density and a low color saturation.

The purpose described above can be achieved by forming an image using an ink set separately having a first ink containing a compound represented by the following general formula (1) and a second ink containing a compound represented by the following general formula (2), i.e., using the first ink and the second ink in combination.

The purpose described above can also be achieved by the use of a thermal transfer recording sheet having a first ink layer containing the compound represented by the following general formula (1) and a second ink layer containing the compound represented by the following general formula (2).

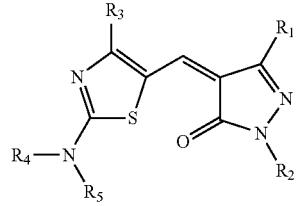

General Formula (1)

[In General Formula (1), $R_1$ represents an alkyl group, an unsubstituted aryl group, an aryl group having a substituent, an acyl group, a carboxy group, an alkoxycarbonyl group, a carboxamide group, an amino group, an alkoxy group, or a cyano group, $R_2$ represents an alkyl group, an unsubstituted aryl group, or an aryl group having a substituent, $R_3$ represents an alkyl group, an unsubstituted aryl group, an aryl group having a substituent, or a heterocyclic group, $R_4$ and $R_5$ each independently represent an alkyl group, and when $R_1$ to $R_3$ are the aryl groups having a substituent, the substituent is an alkyl group, an alkoxy group, or a sulfonic acid salt group.]

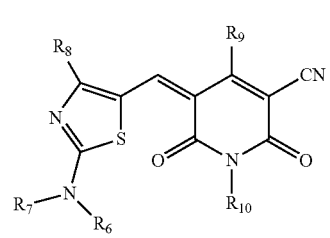

General Formula (2)

[In General Formula (2), $R_6$ and $R_7$ each independently represent an alkyl group, $R_8$ represents an alkyl group or an aryl group, $R_9$ represents an alkyl group, an aryl group, or an amino group, and $R_{10}$ represents a hydrogen atom, an alkyl group, an aryl group, or —N(—$R_{11}$)$R_{12}$, in which $R_{11}$ and $R_{12}$ each independently represent an alkyl group or an acyl group and $R_{11}$ and $R_{12}$ may be bonded to form a ring.]

Further features of the present disclosure will become apparent from the following description of exemplary embodiments.

DESCRIPTION OF THE EMBODIMENTS

Hereinafter, the present disclosure is described in more detail.

The present inventors have conducted an extensive research, and, as a result, have obtained a finding that the problems described above can be solved by forming an image using an ink set separately containing a first ink containing a compound represented by the following general formula (1) and a second ink containing a compound represented by the following general formula (2) to use the first ink and the second ink in combination.

The present inventors have also obtained a finding that the problems described above can be solved by the use of a thermal transfer recording sheet having a first ink layer containing the compound represented by the following general formula (1) and a second ink layer containing the compound represented by the following general formula (2).

First, the compound represented by General Formula (1) is described.

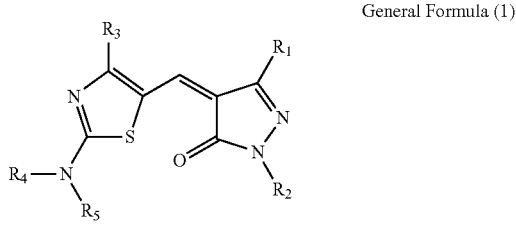

General Formula (1)

[In General Formula (1),
$R_1$ represents an alkyl group, an unsubstituted aryl group, an aryl group having a substituent, an acyl group, a carboxy group, an alkoxycarbonyl group, a carboxamide group, an amino group, an alkoxy group, or a cyano group,
$R_2$ represents an alkyl group, an unsubstituted aryl group, or an aryl group having a substituent,
$R_3$ represents an alkyl group, an unsubstituted aryl group, an aryl group having a substituent, or a heterocyclic group,
$R_4$ and $R_5$ each independently represent an alkyl group, and when $R_1$ to $R_3$ are the aryl groups having a substituent, the substituent is an alkyl group, an alkoxy group, or a sulfonic acid salt group.]

The alkyl group in $R_1$ in General Formula (1) is not particularly limited. Examples of the alkyl group include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. In particular, when alkyl groups having 1 to 4 carbon atoms, such as a methyl group, an ethyl group, an n-propyl group, an iso-propyl group, and an n-butyl group are used, the reproducible color gamut in the red region can be enlarged, and thus the alkyl groups are suitable.

In General Formula (1), as the aryl group in $R_1$, both the unsubstituted aryl group and the aryl group having a substituent can be used. Examples of the substituent include an alkyl group, an alkoxy group, and a sulfonic acid salt group. Specifically, a phenyl group and a naphthyl group are mentioned. In particular, in the case of a phenyl group, the reproducible color gamut in the red region can be enlarged, and thus the phenyl group is suitable.

In General Formula (1), the acyl group in $R_1$ is not particularly limited and an acetyl group, a propionyl group, a benzoyl group, and the like are mentioned, for example.

In General Formula (1), the alkoxycarbonyl group in $R_1$ is not particularly limited and a methoxycarbonyl group, an ethoxycarbonyl group, a propoxycarbonyl group, and the like are mentioned, for example.

In General Formula (1), the carboxamide group in $R_1$ is not particularly limited and a dimethylamide carboxylic acid group, a diethylamide carboxylic acid group, a methylamide carboxylic acid group, an ethylamide carboxylic acid group, and the like are mentioned, for example.

In General Formula (1), the amino group in $R_1$ is not particularly limited and a dialkylamino group, such as a dimethylamino group, a diethylamino group, a dipropylamino group, or a dibutylamino group, a monoalkylamino group, such as a methylamino group, an ethylamino group, a propylamino group, or a butylamino group, a diphenylamino group, a phenylamino group, or the like is mentioned, for example.

In General Formula (1), the alkoxy group in $R_1$ is not particularly limited and a methoxy group, an ethoxy group, a propoxy group, a butoxy group, and the like are mentioned, for example.

The alkyl group in $R_2$ in General Formula (1) is not particularly limited and examples of the alkyl group include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. In particular, when alkyl groups having 1 to 4 carbon atoms, such as a methyl group, an ethyl group, an n-propyl group, an iso-propyl group, and an n-butyl group are used, the reproducible color gamut in the red region can be enlarged, and thus the alkyl groups are suitable.

In General Formula (1), as the aryl group in $R_2$, both the unsubstituted aryl group and the aryl group having a substituent can be used. Examples of the substituent include an alkyl group, an alkoxy group, and a sulfonic acid salt group. Specifically, a phenyl group and a naphthyl group are mentioned. In particular, in the case of a phenyl group, the reproducible color gamut in the red region can be enlarged, and thus the phenyl group is suitable.

The alkyl group in $R_3$ in General Formula (1) is not particularly limited and examples of the alkyl group include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. In particular, when a methyl group is used, the reproducible color gamut in the red region can be enlarged, and thus the methyl group is suitable.

In General Formula (1), as the aryl group in $R_3$, both the unsubstituted aryl group and the aryl group having a substituent can be used. Examples of the substituent include an alkyl group, an alkoxy group, and a sulfonic acid salt group. Specifically, a phenyl group and a naphthyl group are mentioned. In particular, in the case of a phenyl group, the reproducible color gamut in the red region can be enlarged, and thus the phenyl group is suitable.

In General Formula (1), the heterocyclic group in $R_3$ is not particularly limited and a pyridyl group, a thienyl group, and the like are mentioned, for example.

The alkyl groups in $R_4$ and $R_5$ in General Formula (1) are not particularly limited and examples of the alkyl groups include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group.

One aspect of a method for producing the compound having the structure represented by General Formula (1) above of the present disclosure is described below but the production method is not limited thereto.

$R_1$ to $R_5$ in each compound in the reaction formula above and the compound having the structure represented by General Formula (1) are the same as those mentioned above. Moreover, there are cis-trans structural isomers shown in General formulae (1) and (1') and the cis-trans structural isomers fall under the scope of the present disclosure.

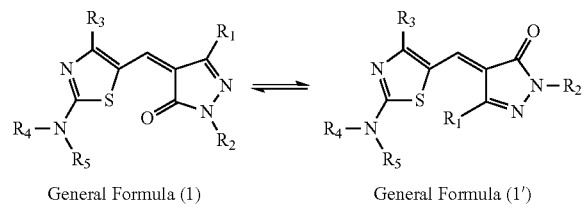

General Formula (1)          General Formula (1')

The compound represented by General Formula (1) of the present disclosure can be easily produced from an ester compound (A).

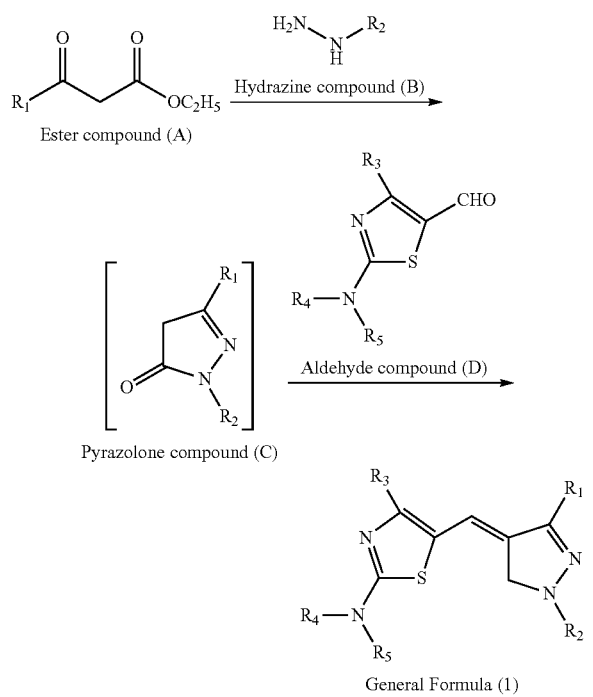

More specifically, an ester compound (A) and a hydrazine compound (B) are reacted to obtain a pyrazolone compound (C), and then an aldehyde compound (D) is subsequently reacted without taking out the pyrazolone compound (C) from a reaction vessel, whereby the compound represented by General Formula (1) can be obtained.

For example, the compound represented by General Formula (1) can be produced with reference to known methods of Journal of Medicinal Chemistry, Vol. 44, No. 22, pp. 3730-3745 (2001), for example.

Various kinds of the ester compound (A) and the hydrazine compound (B) are commercially available, and thus can be easily obtained. Alternatively, the ester compound (A) and the hydrazine compound (B) can be easily synthesized by known methods (for example, JIKKEN KAGAKU KOZA (Experimental Chemistry Course) 14. YUKI KAGOBUTSU NO GOSEI TO HANNO (Synthesis and Reaction of Organic Compound) [III], pp. 1573 to 1584). Although not particularly limited, specific examples thereof include, for example, methylhydrazine, ethylhydrazine, n-propylhydrazine, isopropylhydrazine, n-butylhydrazine, isobutylhydrazine, sec-butylhydrazine, tert-butylhydrazine, cyclopropylhydrazine, cyclobutylhydrazine, cyclopentylhydrazine, phenylhydrazine, phenethylhydrazine, naphthylhydrazine, benzylhydrazine, and the like.

This reaction can be performed in the absence of solvent but is suitably performed in the presence of solvent. The solvent to be used is not particularly limited insofar as the reaction is not blocked. Examples of the solvent include, for example, water, alcohols, such as methanol, ethanol, and propyl alcohol, esters, such as methyl acetate, ethyl acetate, and propyl acetate, ethers, such as diethylether, tetrahydrofuran, and dioxane, aromatic hydrocarbon solvents, such as benzene, toluene, and xylene, amides, such as N,N-dimethylformamide and N,N-dimethylimidazolidinone, nitriles, such as acetonitrile and propionitrile, and acids, such as hydrochloric acid, formic acid, acetic acid, and propionic acid. Two or more kinds of the solvents can be mixed for use and the mixing ratio in the case of using the mixture can be arbitrarily determined. The use amount of the solvent to be used in the present disclosure is in the range of 0.1 to 1000 mass times, preferably 0.5 to 100 mass times, and more preferably 1.0 to 20 mass times the use amount of the ester compound (A).

As the reaction temperature, the reaction is performed at a temperature range of −80° C. to 250° C., preferably −50° C. to 200° C., and more preferably −20° C. to 150° C. In usual, the reaction is completed within 24 hours.

After the completion of the reaction, an aldehyde compound (D) is allowed to act.

The aldehyde compound (D) can be synthesized referring to a known method described in WO92/19684.

As suitable examples of the aldehyde compound (D), aldehyde compounds (1) to (8) are shown below but the aldehyde compound (D) is not limited to the following compounds.

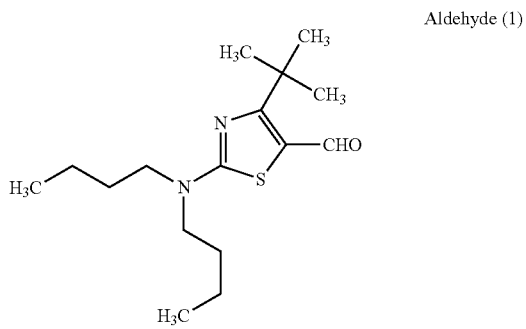

Aldehyde (1)

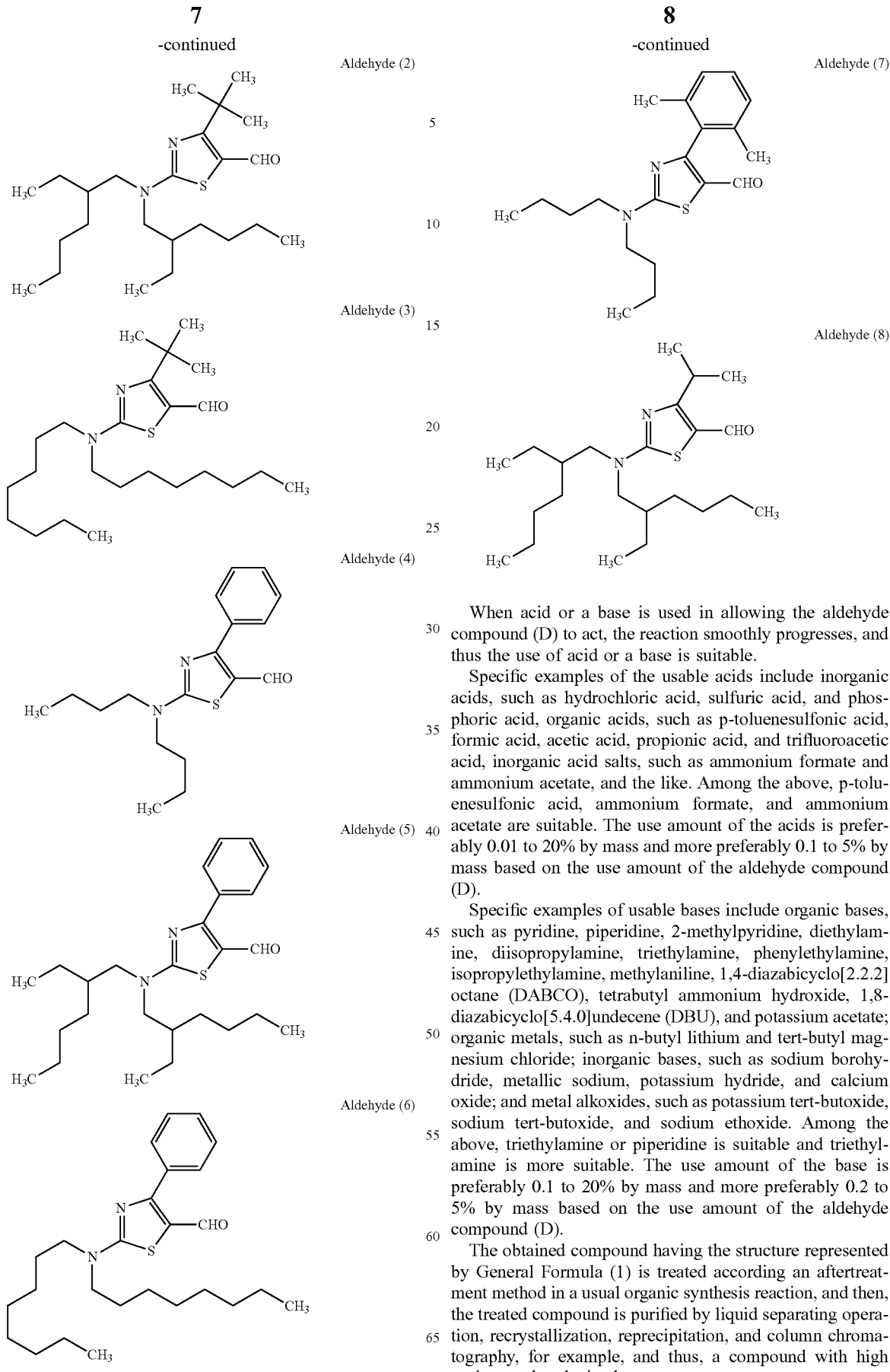

When acid or a base is used in allowing the aldehyde compound (D) to act, the reaction smoothly progresses, and thus the use of acid or a base is suitable.

Specific examples of the usable acids include inorganic acids, such as hydrochloric acid, sulfuric acid, and phosphoric acid, organic acids, such as p-toluenesulfonic acid, formic acid, acetic acid, propionic acid, and trifluoroacetic acid, inorganic acid salts, such as ammonium formate and ammonium acetate, and the like. Among the above, p-toluenesulfonic acid, ammonium formate, and ammonium acetate are suitable. The use amount of the acids is preferably 0.01 to 20% by mass and more preferably 0.1 to 5% by mass based on the use amount of the aldehyde compound (D).

Specific examples of usable bases include organic bases, such as pyridine, piperidine, 2-methylpyridine, diethylamine, diisopropylamine, triethylamine, phenylethylamine, isopropylethylamine, methylaniline, 1,4-diazabicyclo[2.2.2]octane (DABCO), tetrabutyl ammonium hydroxide, 1,8-diazabicyclo[5.4.0]undecene (DBU), and potassium acetate; organic metals, such as n-butyl lithium and tert-butyl magnesium chloride; inorganic bases, such as sodium borohydride, metallic sodium, potassium hydride, and calcium oxide; and metal alkoxides, such as potassium tert-butoxide, sodium tert-butoxide, and sodium ethoxide. Among the above, triethylamine or piperidine is suitable and triethylamine is more suitable. The use amount of the base is preferably 0.1 to 20% by mass and more preferably 0.2 to 5% by mass based on the use amount of the aldehyde compound (D).

The obtained compound having the structure represented by General Formula (1) is treated according an aftertreatment method in a usual organic synthesis reaction, and then, the treated compound is purified by liquid separating operation, recrystallization, reprecipitation, and column chromatography, for example, and thus, a compound with high purity can be obtained.

The compounds having the structure represented by General Formula (1) may be used alone or in combination of two or more kinds thereof in order to adjust the color tone and the like according to the purpose of the application. Furthermore, two or more kinds of known pigments or dyes may be used in combination.

As suitable examples of the compound represented by General Formula (1), compounds (1) to (31) are shown below but the compound represented by General Formula (1) is not limited to the following compounds.

Compound (1)

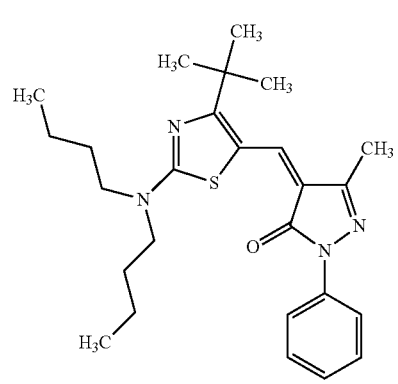

Compound (2)

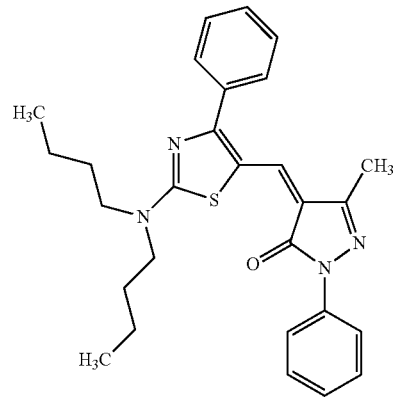

Compound (3)

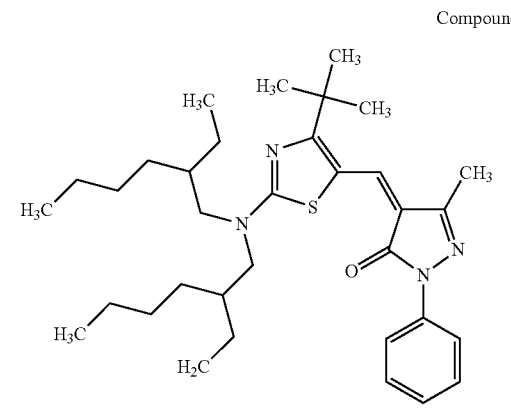

-continued

Compound (4)

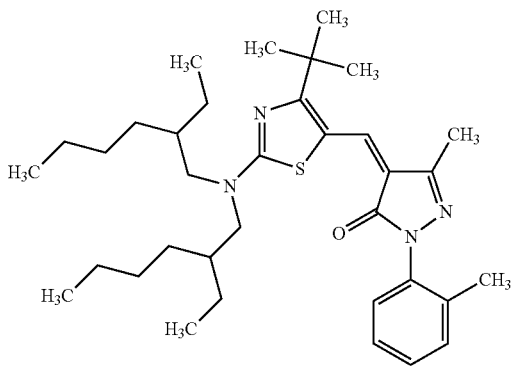

Compound (5)

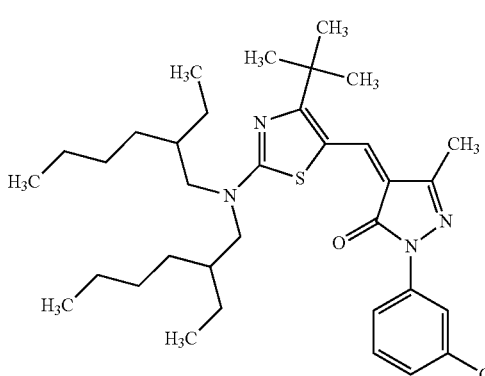

Compound (6)

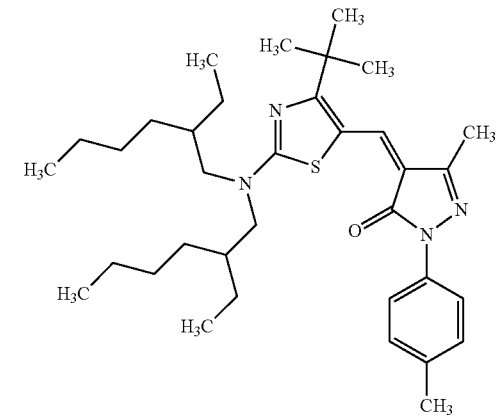

Compound (7)

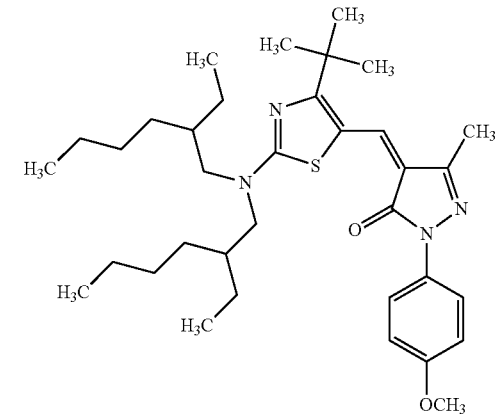

Compound (8)
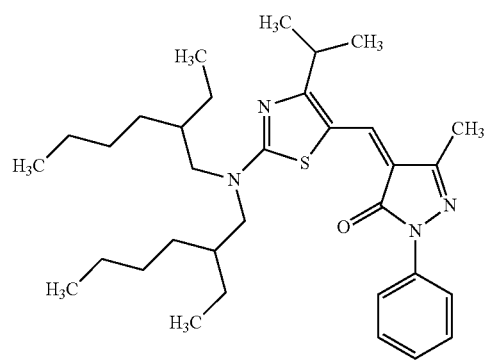
Compound (9)
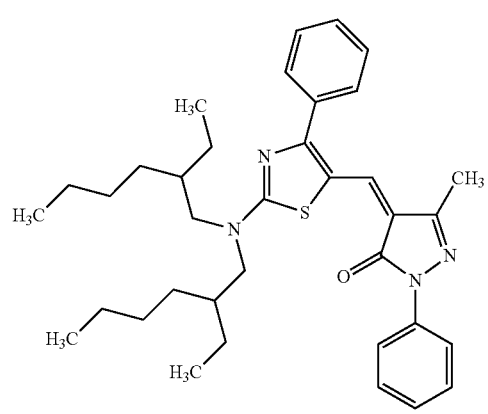
Compound (10)
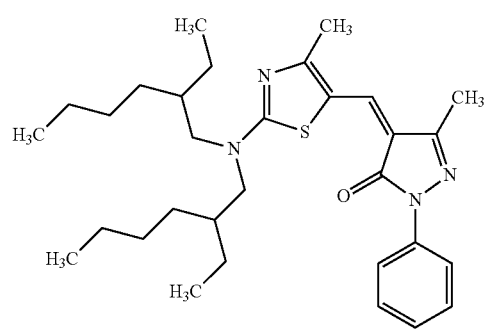
Compound (11)
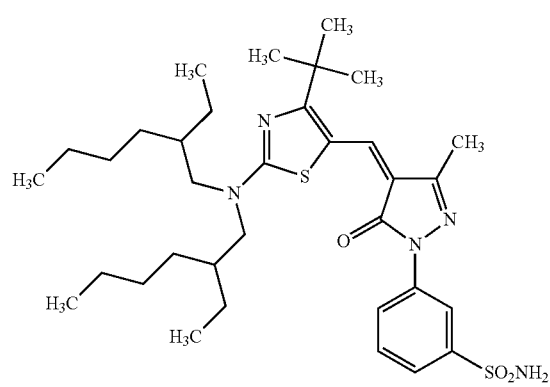
Compound (12)
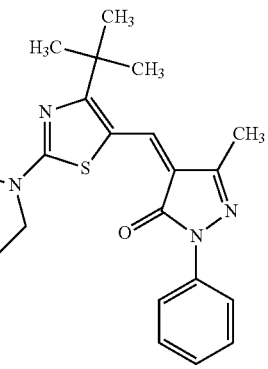
Compound (13)
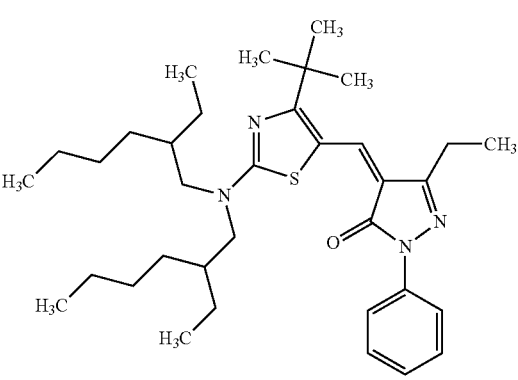
Compound (14)
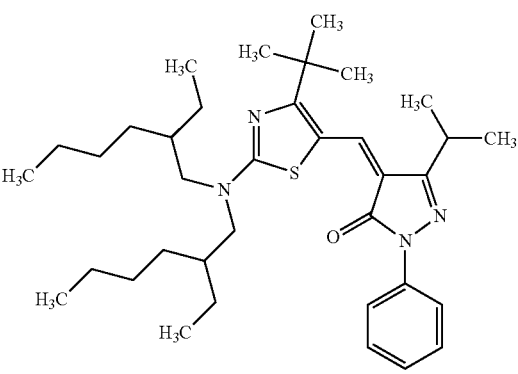
Compound (15)
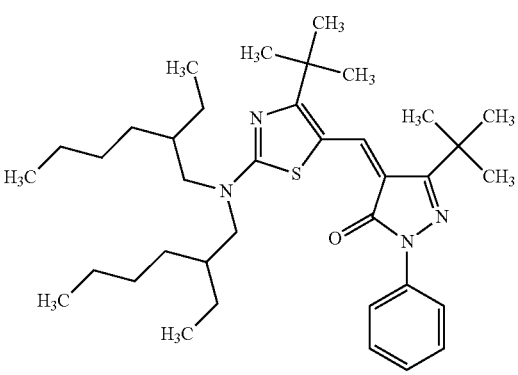

Compound (16)
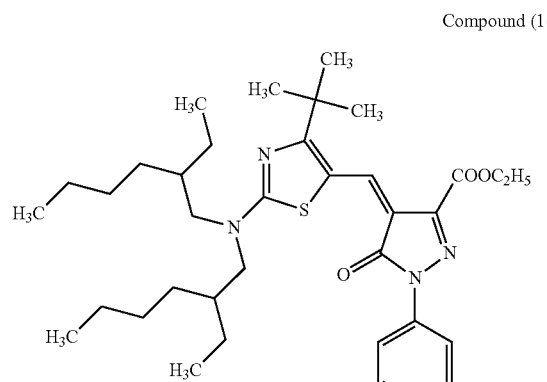
Compound (17)
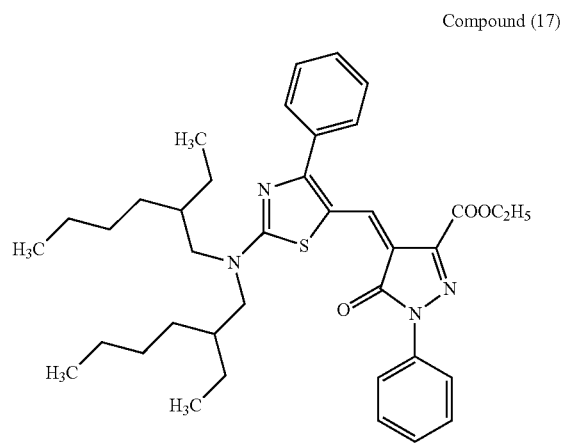
Compound (18)
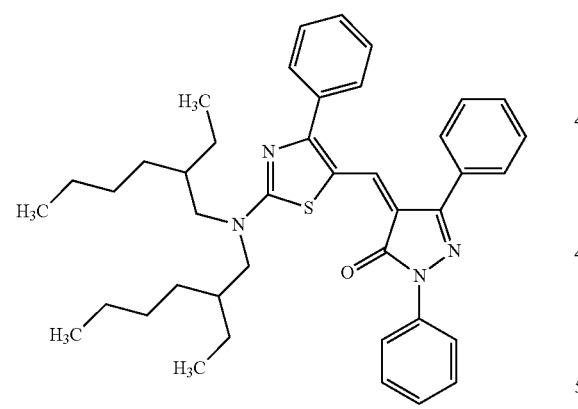
Compound (19)
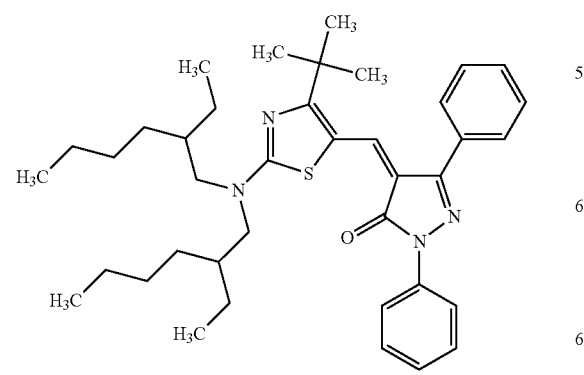
Compound (20)
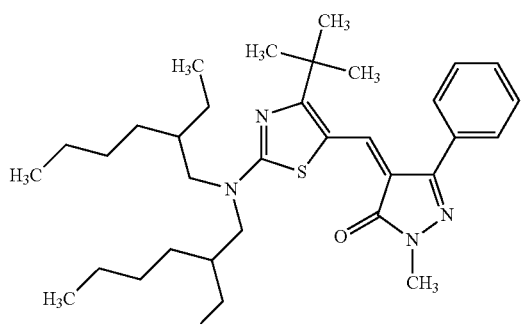
Compound (21)
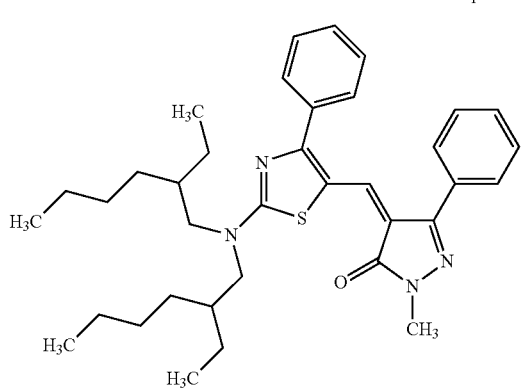
Compound (22)
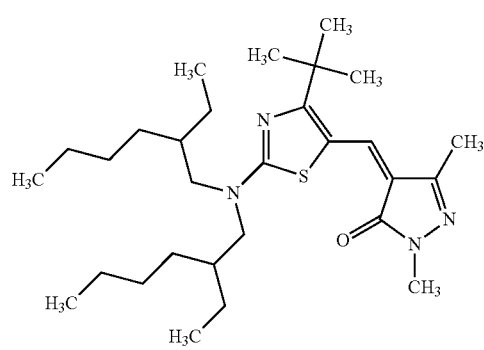
Compound (23)
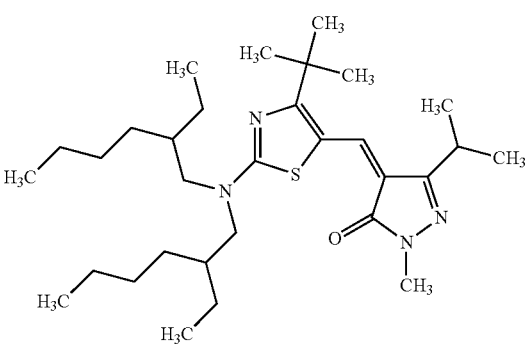

Compound (24)
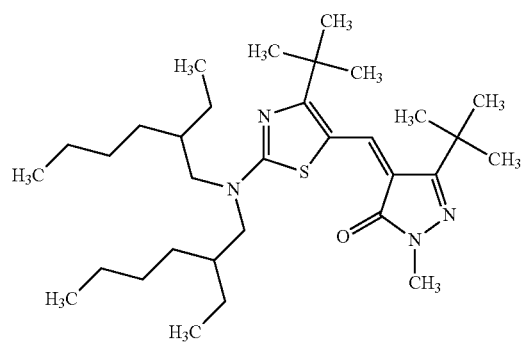
Compound (25)
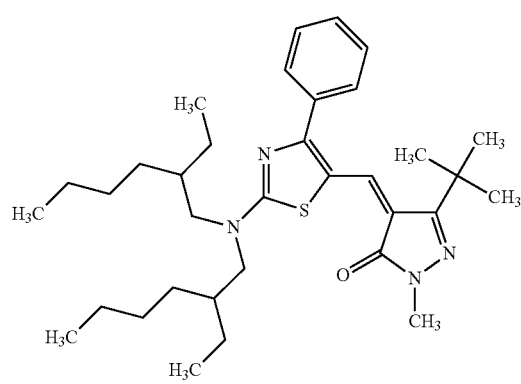
Compound (26)
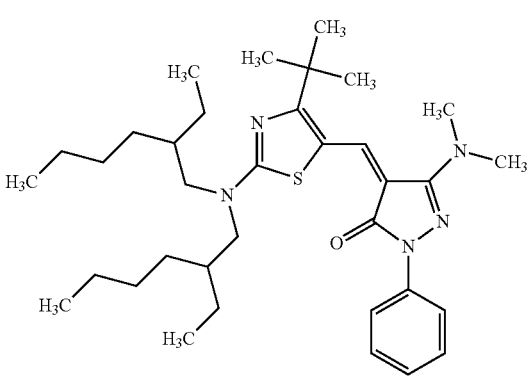
Compound (27)
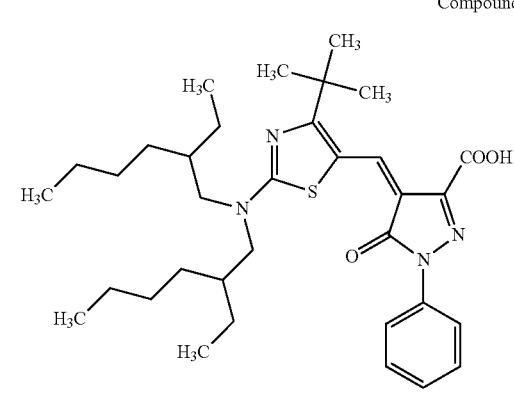
Compound (28)
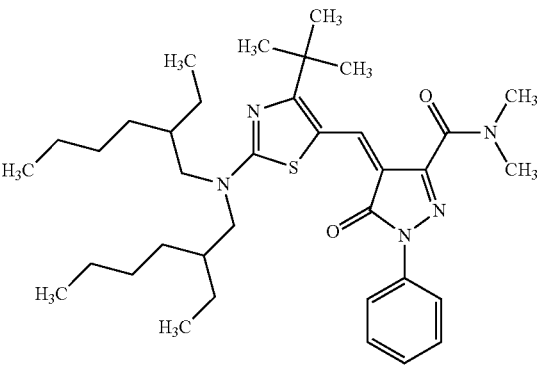
Compound (29)
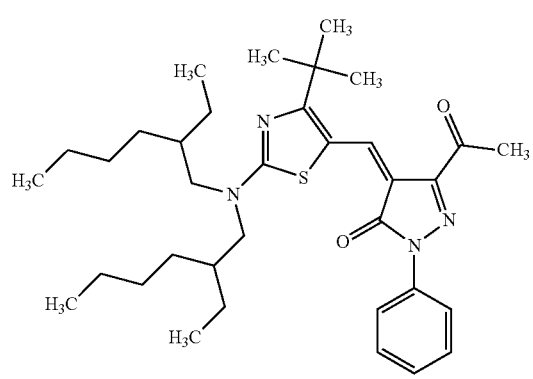
Compound (30)
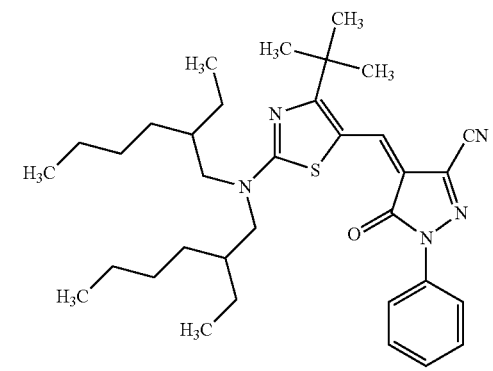
Compound (31)
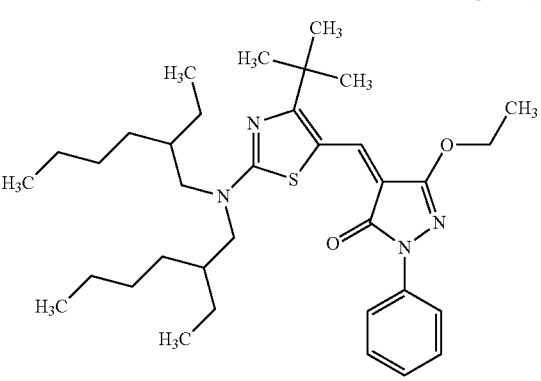
Among the above, suitable compounds are the compounds (1), (3), (6), (7), (9), (11), (14), (16), (19), (20), (22), and (31). In particular, the compounds (1), (3), (6), (14), (20), and (31) are suitable because the effects of the present disclosure become more remarkable.

The compound represented by General Formula (2) is described.

General Formula (2)

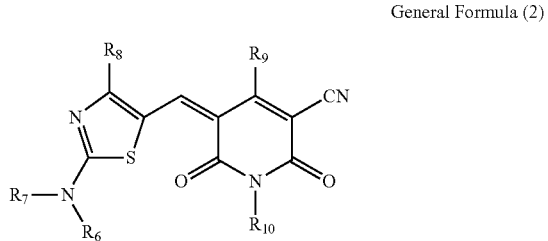

[In General Formula (2), $R_6$ and $R_7$ each independently represent an alkyl group, $R_8$ represents a hydrogen atom, an alkyl group, an unsubstituted aryl group, or an aryl group having a substituent, $R_9$ represents an alkyl group, an unsubstituted aryl group, or an aryl group having a substituent, $R_{10}$ represents a hydrogen atom, an alkyl group, an unsubstituted aryl group, an aryl group having a substituent, or —N(—$R_{11}$)$R_{12}$, in which $R_{11}$ and $R_{12}$ each independently represent a hydrogen atom, an alkyl group, or an acyl group and $R_{11}$ and $R_{12}$ may be bonded to form a ring, and when $R_8$ to $R_{10}$ are the aryl groups having a substituent, the substituent is an alkyl group or an alkoxy group.]

In General Formula (2), the alkyl groups in $R_6$ and $R_7$ are not particularly limited and examples of the alkyl groups include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. In particular, when the branched alkyl group, such as a 2-ethylhexyl group, is used, the reproducible color gamut in the red region can be enlarged and black color with high density and low color saturation can be represented.

In General Formula (2), the alkyl group in $R_8$ is not particularly limited and examples of the alkyl group include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. Particularly in the case of a tert-butyl group, the reproducible color gamut in the red region can be enlarged and black color with high density and low color saturation can be represented.

In General Formula (2), as the aryl group in $R_8$, both the unsubstituted aryl group and the aryl group having a substituent can be used. For example, an unsubstituted phenyl group and a phenyl group having a substituent are mentioned. Examples of the substituent include an alkyl group, an alkoxy group, and a sulfonic acid salt group. Specifically, a phenyl group, a 2-methylphenyl group, a 3-methylphenyl group, a 4-methylphenyl group, a 2,6-dimethylphenyl group, a 2,6-diethylphenyl group, a 2,6-dimethoxy phenyl group, a 2,4,6-trimethylphenyl group, a 2,4,6-triethylphenyl group, and a 3-methoxy phenyl group are mentioned.

$R_8$ is suitably an unsubstituted phenyl group or a tert-butyl group and most suitably a tert-butyl group. In this case, the effects of the present disclosure become more remarkable.

In General Formula (2), the alkyl group in $R_9$ is not particularly limited and alkyl groups having 1 to 4 carbon atoms, such as a methyl group, an ethyl group, an n-propyl group, an iso-propyl group, an n-butyl group, an iso-butyl group, a 2-methylbutyl group, and a 2,3,3-trimethylbutyl group are mentioned, for example. Particularly in the case of a methyl group, the reproducible color gamut in the red region can be enlarged and black color with high density and low color saturation can be represented.

In General Formula (2), as the aryl group in $R_9$, an unsubstituted aryl group and an aryl group having a substituent can be used. Examples of the substituent in this case include an alkyl group and an alkoxy group. For example, a phenyl group, a 2-methylphenyl group, a 3-methylphenyl group, a 4-methylphenyl group, a 4-methoxyphenyl group, 3, and a 3,5-dimethylphenyl group are mentioned.

In General Formula (2), the alkyl group in $R_{10}$ is not particularly limited and a methyl group, an ethyl group, an n-propyl group, an iso-propyl group, an n-butyl group, and an iso-butyl group are mentioned, for example. Particularly in the case of a methyl group, the reproducible color gamut in the red region can be enlarged and black color with high density and low color saturation can be represented.

In General Formula (2), as the aryl group in $R_{10}$, both the unsubstituted aryl group and the aryl group having a substituent can be used. Examples of the substituent in this case include an alkyl group and an alkoxy group. For example, an unsubstituted phenyl group and a phenyl group having a substituent are mentioned.

When $R_{10}$ is —N($R_{11}$)$R_{12}$, the alkyl groups in $R_{11}$ and $R_{12}$ are not particularly limited and examples of the alkyl groups include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. Particularly in the case of a methyl group, the reproducible color gamut in the red region can be enlarged and black color with high density and low color saturation can be represented.

When $R_{10}$ is —N($R_{11}$)$R_{12}$, the acyl groups in $R_{11}$ and $R_{12}$ are not particularly limited and a formyl group, substituted or unsubstituted alkyl carbonyl groups having 2 to 30 carbon atoms, substituted or unsubstituted aryl carbonyl groups having 7 to 30 carbon atoms, and a heterocyclic carbonyl group are mentioned, for example. Specifically, an acetyl group, a propionyl group, a pivaloyl group, a benzoyl group, a naphthoyl group, a 2-pyridyl carbonyl group, and a 2-furyl carbonyl group are mentioned.

In General Formula (2), the ring formed by bonding of $R_{11}$ and $R_{12}$ is not particularly limited and a piperidine ring, a piperazine ring, and a morpholine ring are mentioned.

Particularly when at least either $R_{11}$ or $R_{12}$ is an alkyl group, particularly in the case of a methyl group, the reproducible color gamut in the red region can be enlarged and black color with high density and low color saturation can be represented.

The compound having the structure represented by General Formula (2) according to the present disclosure can be synthesized referring to a known method described in WO92/19684. General formula (2) has cis-trans structural isomers and the cis-trans structural isomers fall under the scope of the present disclosure.

As suitable examples of the compound represented by General Formula (2), compounds (32) to (60) are shown below but the compound represented by General Formula (2) is not limited to the following compounds.

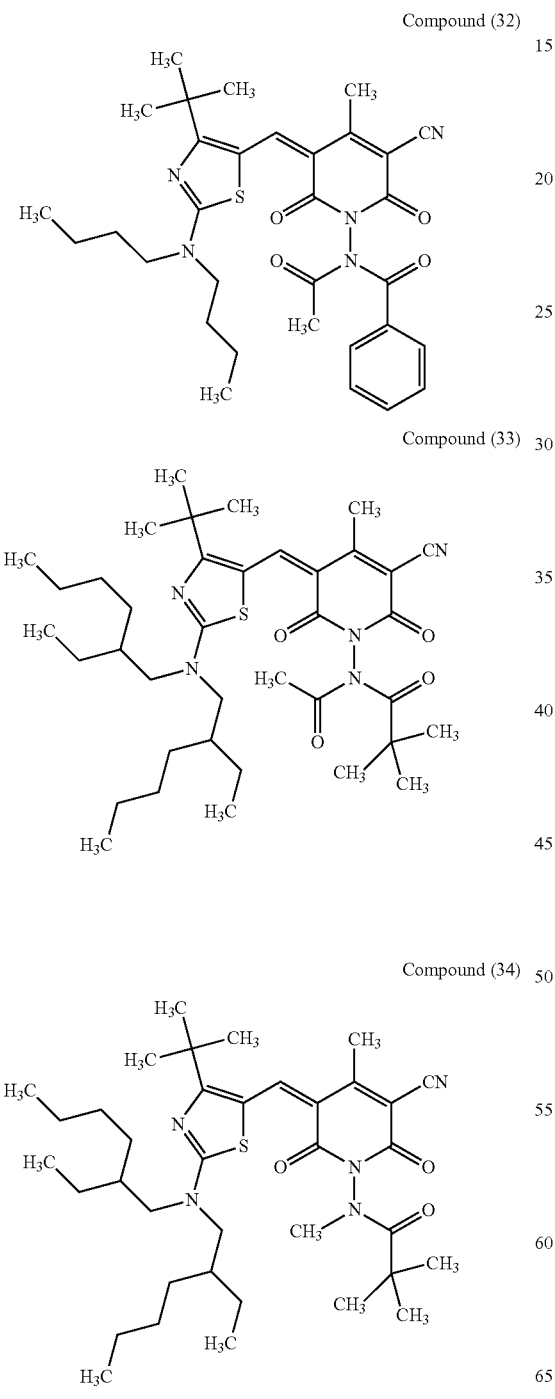

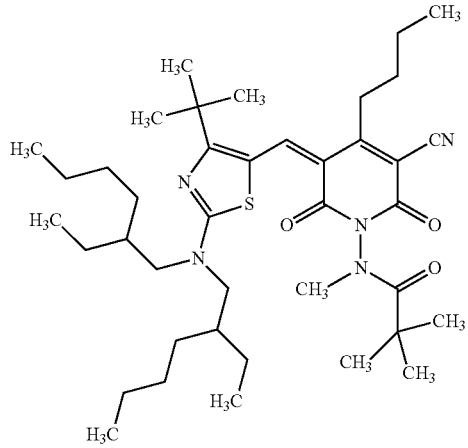

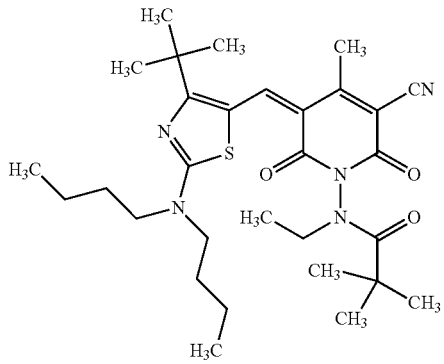

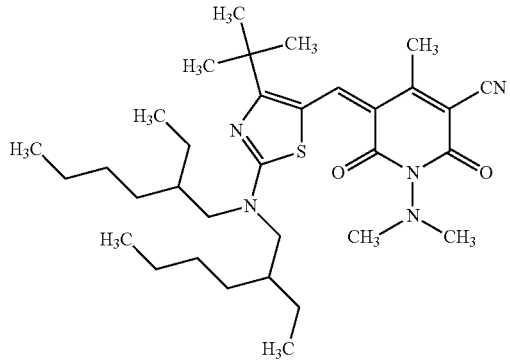

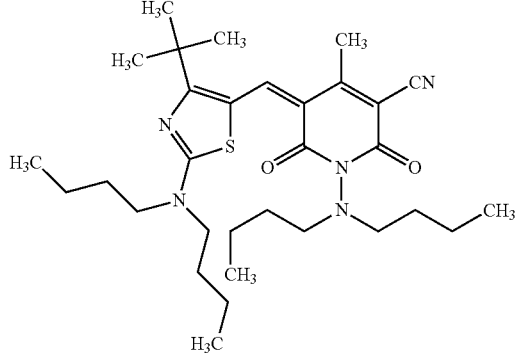

Compound (39)
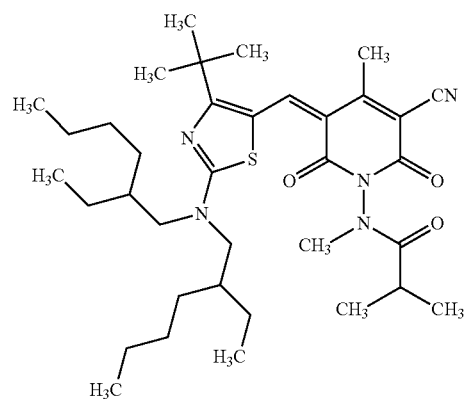
Compound (40)
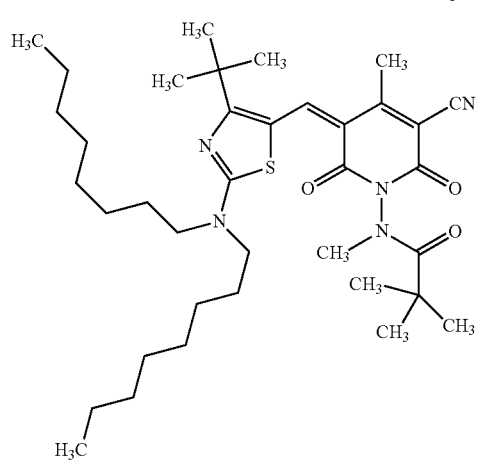
Compound (41)
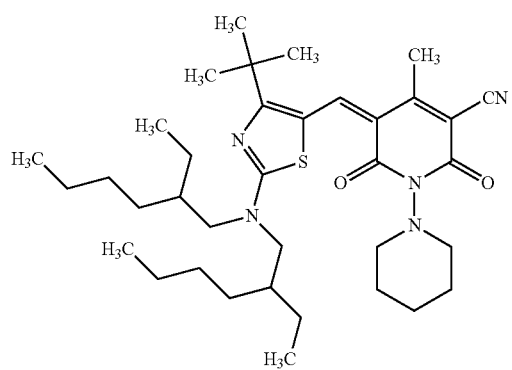
Compound (42)
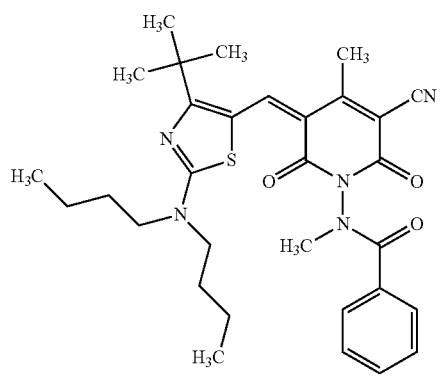
Compound (43)
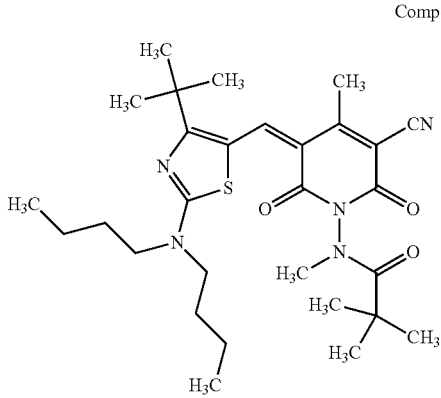
Compound (44)
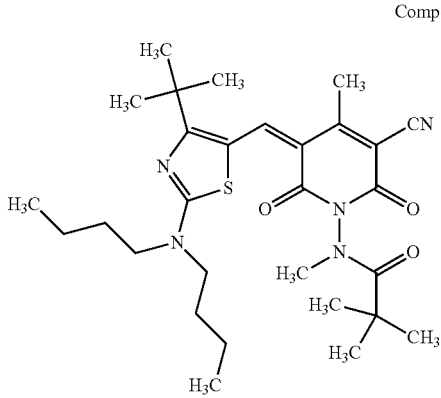

Compound (45)
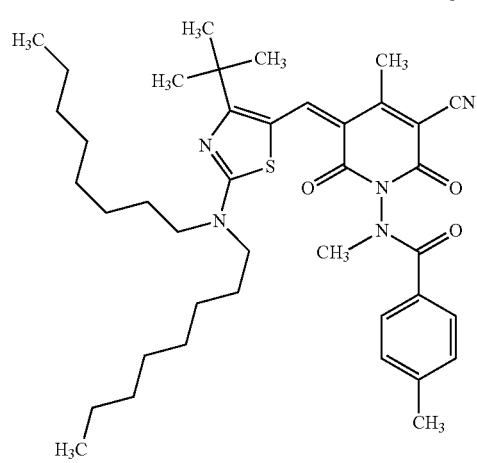
Compound (46)
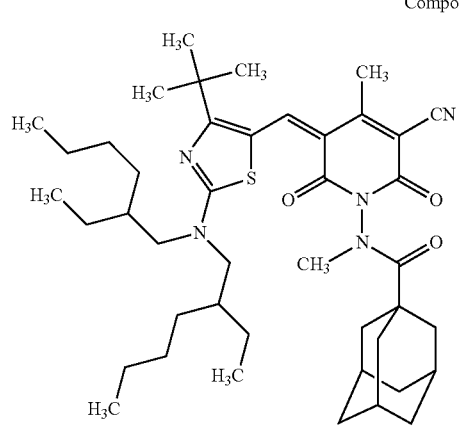
Compound (47)
Compound (48)
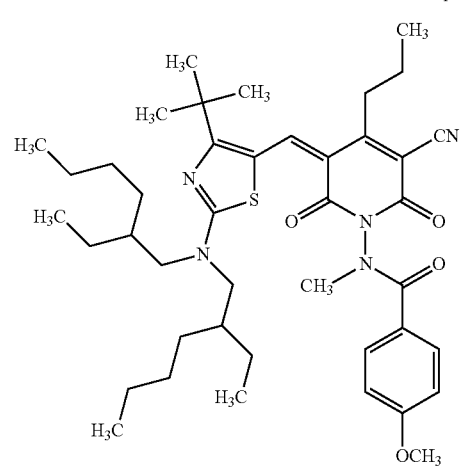
Compound (49)
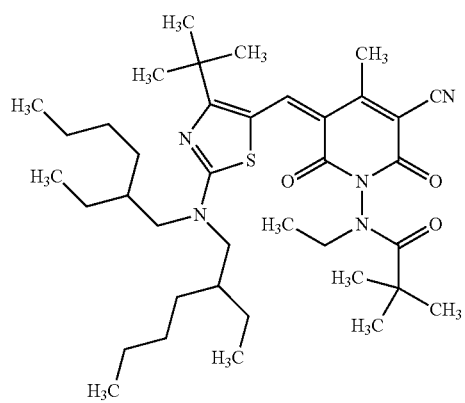
Compound (50)
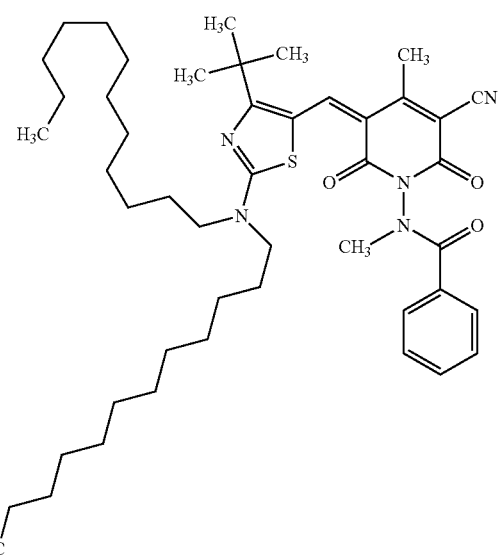

Compound (51)
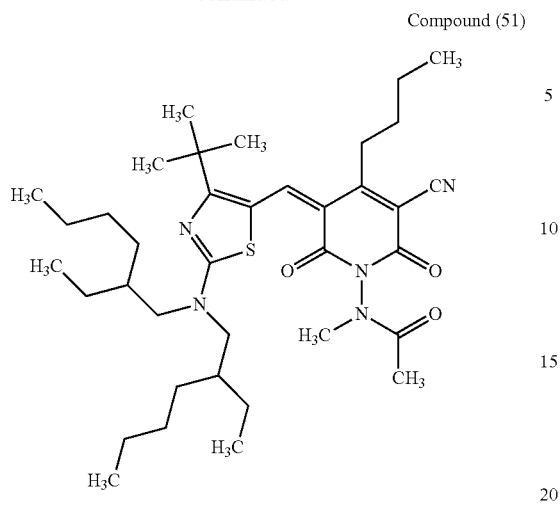
Compound (52)
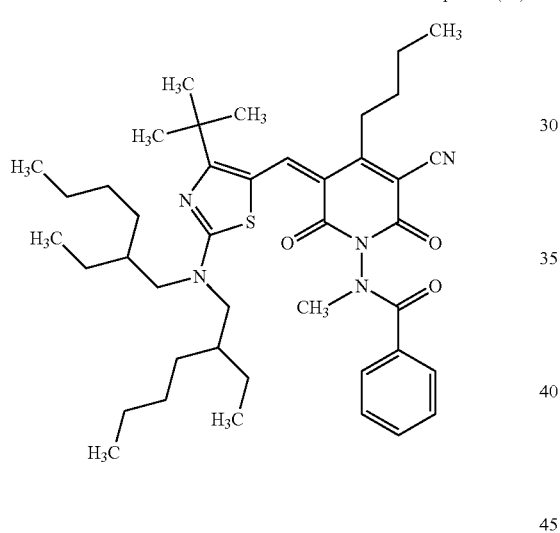
Compound (53)
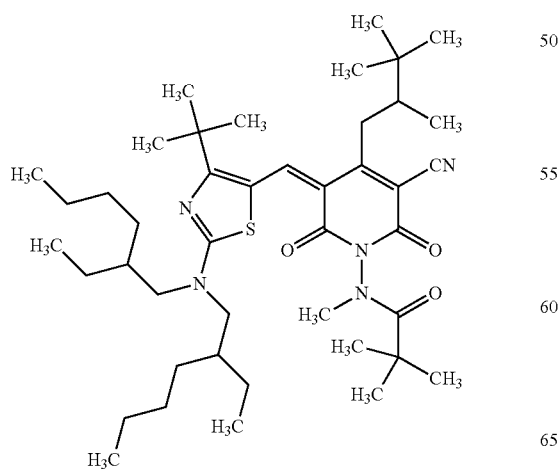
Compound (54)
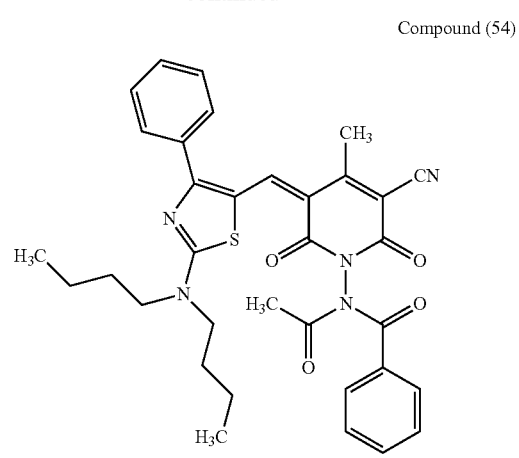
Compound (55)
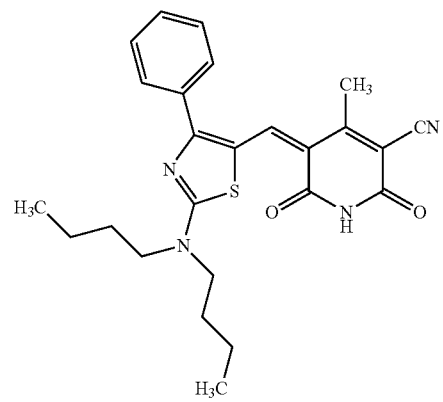
Compound (56)
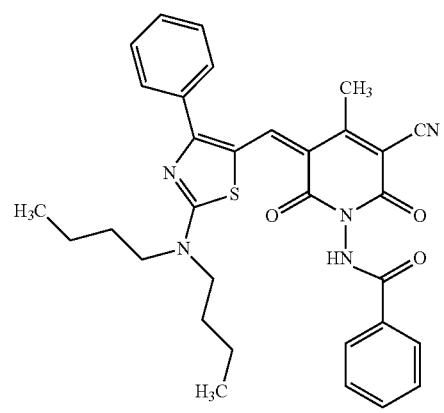

Compound (57)

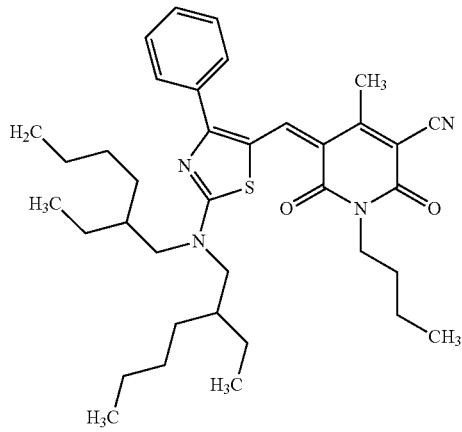

Compound (58)

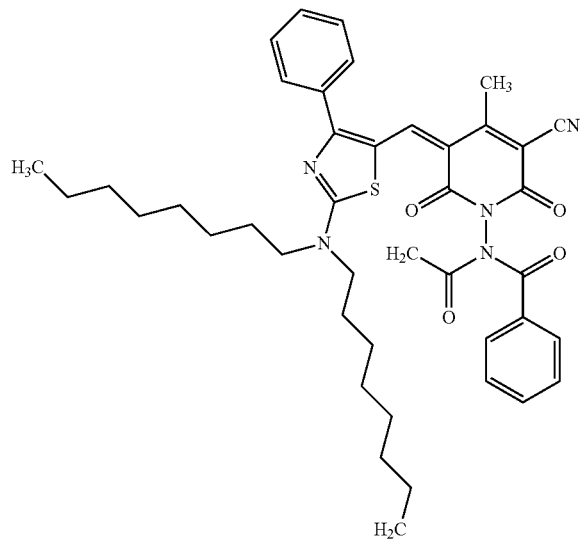

Compound (59)

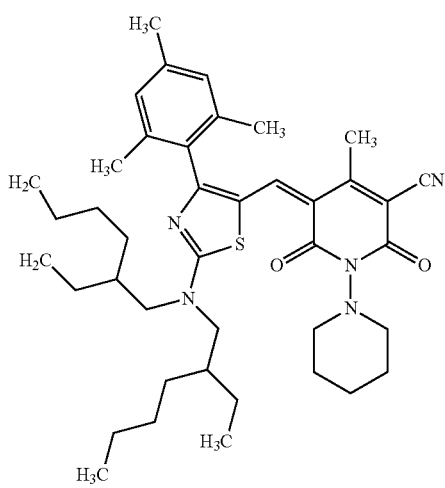

Compound (60)

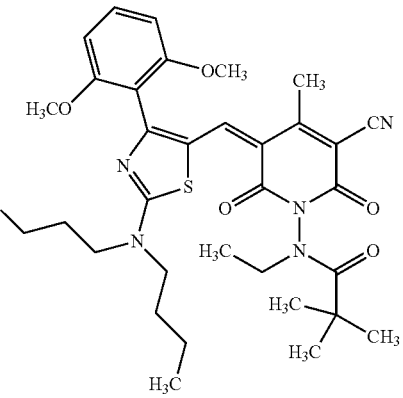

Among the above, suitable compounds are the compounds (32), (34), (37), (42), (44), (52), and (54). The compounds (32), (34), (42), and (44) are particularly suitable and, in this case, the effects of the present disclosure become more remarkable.

In the present disclosure, at least either the first ink or the second ink may further contain a compound selected from the group consisting of compounds represented by the following general formulae (3) to (13).

First, the compound represented by General Formula (3) is described.

General Formula (3)

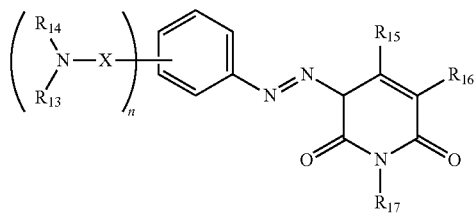

In General Formula (3),
either $R_{13}$ or $R_{14}$ represents an alkyl group and the other one represents a hydrogen atom or an alkyl group,
$R_{15}$ represents an alkyl group, an unsubstituted aryl group, an aryl group having a substituent, or an amino group,
$R_{16}$ represents a hydrogen atom, a cyano group, a carbamoyl group, an alkoxycarbonyl group, or a carboxamide group,
$R_{17}$ represents a hydrogen atom, an alkyl group, an unsubstituted aryl group, an aryl group having a substituent, or —N(—$R_{18}$)$R_{19}$, in which $R_{18}$ and $R_{19}$ each independently represent a hydrogen atom, an alkyl group, or an acyl group and $R_{18}$ and $R_{19}$ may be bonded to each other to form a ring, when $R_{15}$ and $R_{17}$ are the aryl groups having a substituent, the substituent is an alkyl group,
X represents a carbonyl group or a sulfonyl group, and
n represents an integer of 1 to 3.

In General Formula (3), the alkyl groups in $R_{13}$ and $R_{14}$ are not particularly limited and examples of the alkyl group include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group.

Among the above, it is suitable that $R_{13}$ and $R_{14}$ each independently represent an ethyl group, an n-butyl group, a sec-butyl group, a dodecyl group, a cyclohexyl group, a methylcyclohexyl group, 2-ethylpropyl, a 2-ethylhexyl group, or a cyclohexenylethyl group because the lightfastness is excellent and it is more suitable that $R_{13}$ and $R_{14}$ each independently represent an n-butyl group or a 2-ethylhexyl group. Moreover, it is suitable that $R_{13}$ and $R_{14}$ represent the same alkyl group because high color saturation and wide color gamut reproducibility are imparted and high grade process black can be represented.

In General Formula (3), the alkyl group in $R_{15}$ is not particularly limited and a methyl group, an ethyl group, a propyl group, and a butyl group are mentioned.

In General Formula (3), the aryl group in $R_{15}$ may be unsubstituted or may have a substituent, and an alkyl group is mentioned as the substituent in this case. For example, a phenyl group and a methylphenyl group are mentioned.

In General Formula (3), the amino group in $R_{15}$ is not particularly limited and an amino group and a dimethylamino group are mentioned.

Among the above, when $R_{15}$ is an alkyl group, the reproducible color gamut in the red region can be expanded and black color with high density and low color saturation can be represented. A methyl group is more suitable.

In General Formula (3), the alkoxycarbonyl group in $R_{16}$ is not particularly limited and a methoxycarbonyl group and an ethoxycarbonyl group are mentioned.

In General Formula (3), examples of the carboxamide group in $R_{16}$ include carboxy dialkylamide groups, such as a carboxy dimethylamide group and a carboxy diethylamide group, and carboxy monoalkylamide groups, such as a carboxy methylamide group and a carboxy ethylamide group.

In General Formula (3), when $R_{16}$ is a cyano group, the reproducible color gamut in the red region can be enlarged and black color with high density and low color saturation can be represented.

In General Formula (3), the alkyl group in $R_{17}$ is not particularly limited and examples of the alkyl group include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. A methyl group, an ethyl group, an n-propyl group, an iso-propyl group, an n-butyl group and a 2-ethylhexyl group are suitable. Particularly in the case of an ethyl group and an n-propyl group, the reproducible color gamut in the red region can be enlarged and black color with high density and low color saturation can be represented.

In General Formula (3), the aryl group in $R_{17}$ may be unsubstituted or may have a substituent, and an alkyl group is mentioned as the substituent in this case. For example, a phenyl group and a methylphenyl group are mentioned.

In General Formula (3), the alkyl groups in $R_{18}$ and $R_{19}$ are not particularly limited and examples of the alkyl groups include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group.

In General Formula (3), the acyl groups in $R_{18}$ and $R_{19}$ are not particularly limited and a formyl group, an acetyl group, an ethylhexanoyl group, and a benzoyl group are mentioned.

Particularly when at least either $R_{18}$ or $R_{19}$ is an alkyl group, the effects of the present disclosure become more remarkable, and thus the case is suitable. In particular, a methyl group is suitable.

In General Formula (3), the ring formed by bonding of $R_{18}$ and $R_{19}$ is not particularly limited insofar as high color saturation and wide color gamut reproducibility are imparted and the representation of high grade process black is not adversely affected. A pyrrolidine ring, a piperidine ring, an azepane ring, and an azocane ring are mentioned.

In General Formula (3), when X represents a carbonyl group, the reproducible color gamut in the red region can be enlarged and black color with high density and low color saturation can be represented.

In General Formula (3), n is suitably an integer of 1 to 3. In this case, the effects of the present disclosure become more remarkable. In particular, n is suitably 1.

General Formula (3) shows the azo form, and a tautomer which is a hydrazo form also falls under the scope of the present disclosure.

The compound having the structure represented by General Formula (3) can be synthesized referring to a known method described in WO08/114886.

Suitable examples of the compound represented by General Formula (3), compounds (61) to (71) are shown below but the compound is not limited to the following compounds.

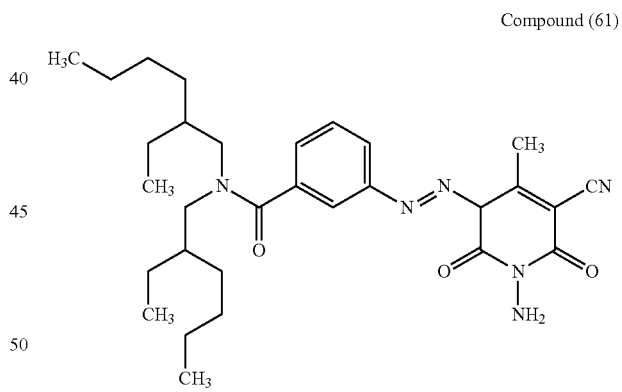

Compound (61)

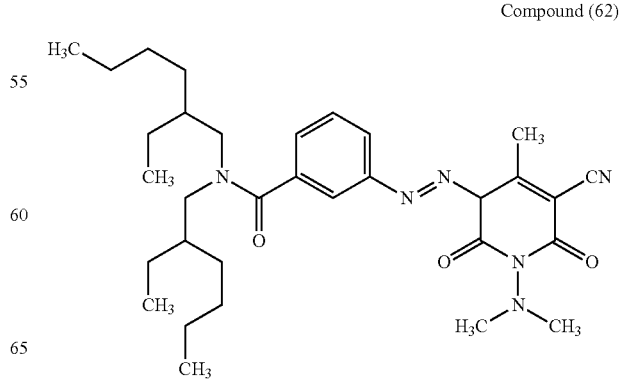

Compound (62)

Compound (63)
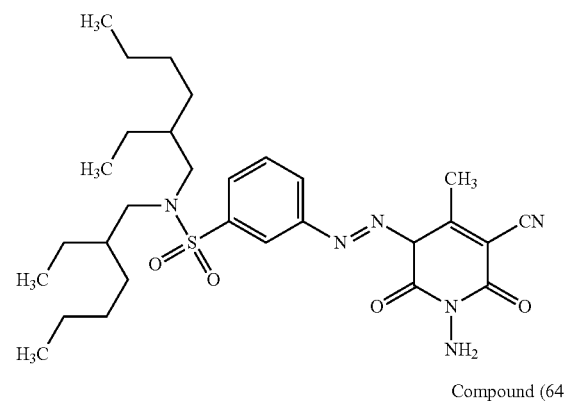
Compound (64)
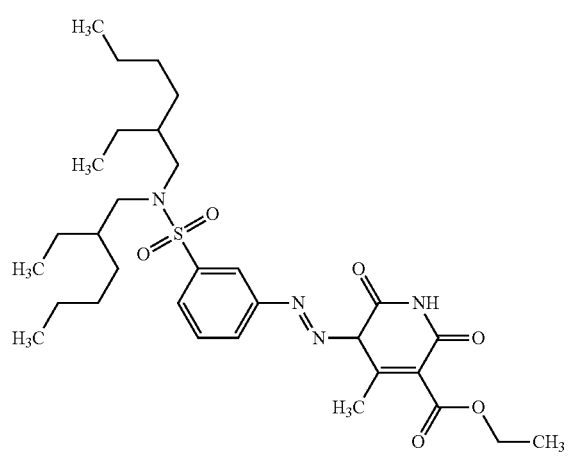
Compound (65)
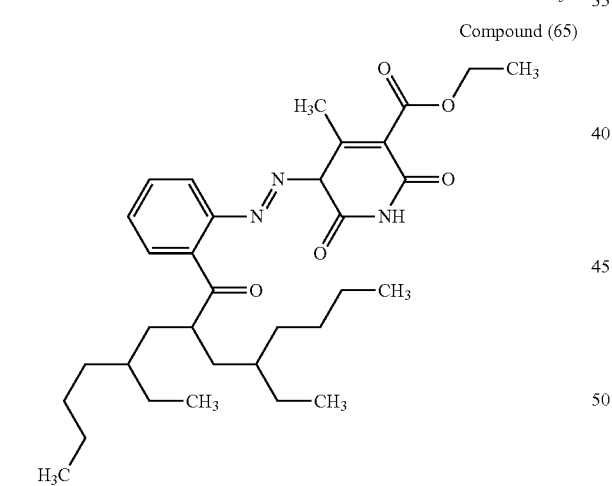
Compound (66)
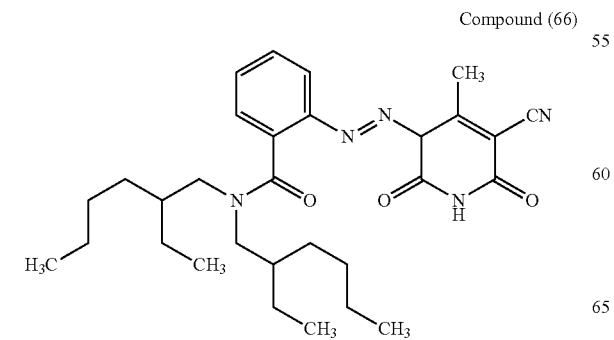
Compound (67)
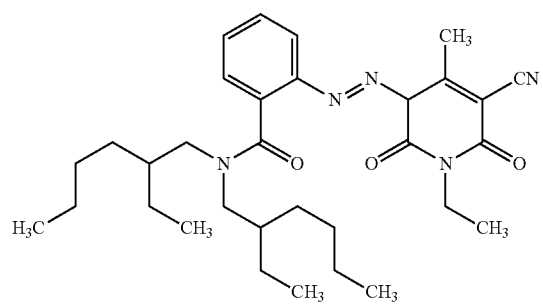
Compound (68)
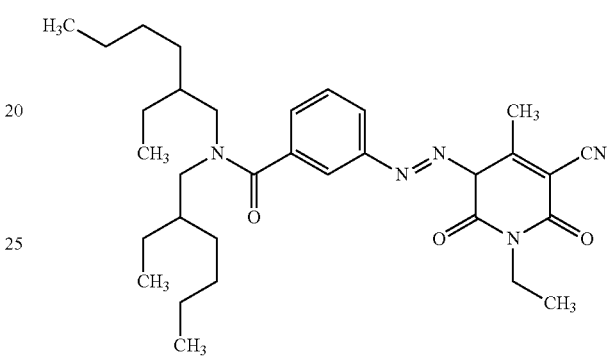
Compound (69)
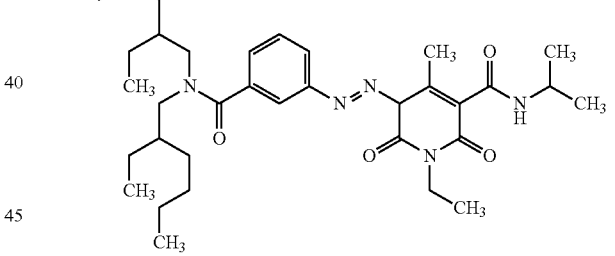
Compound (70)
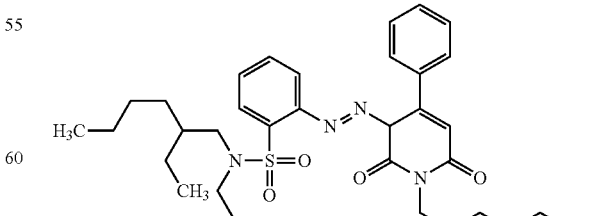

Compound (71)

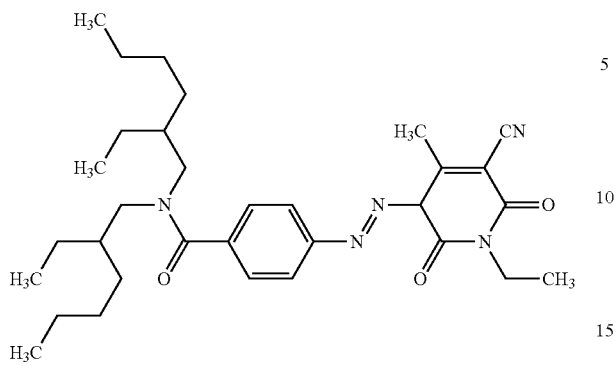

Among the above, suitable compounds are the compounds (62), (63), (67), (68), and (71). The compounds (67), (68), and (71) are particularly suitable and the effects of the present disclosure become more remarkable in this case.

Next, a compound represented by General Formula (4) is described.

General Formula (4)

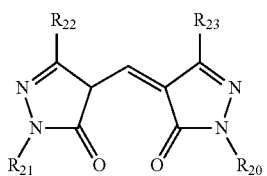

[In General Formula (4), $R_{20}$ to $R_{23}$ each independently represent an alkyl group, an unsubstituted aryl group, or an aryl group having a substituent. When $R_{20}$ to $R_{23}$ are the aryl groups having a substituent, the substituent is an alkyl group or an alkoxy group.]

In General Formula (4), the alkyl groups in $R_{20}$ to $R_{23}$ are not particularly limited and examples of the alkyl groups include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. Particularly when alkyl groups having 1 to 2 carbon atoms, such as a methyl group and an ethyl group, are used, the reproducible color gamut in the red region can be enlarged and black color with high density and low color saturation can be represented.

In General Formula (4), the aryl groups in $R_{20}$ to $R_{23}$ may be unsubstituted or may have a substituent. When $R_{20}$ to $R_{23}$ are the aryl groups having a substituent, the substituent is an alkyl group or an alkoxy group. For example, a phenyl group and a naphthyl group are mentioned. Particularly in the case of using a phenyl group, the reproducible color gamut in the red region can be enlarged and black color with high density and low color saturation can be represented.

Suitable examples of the compound represented by General Formula (4), compounds (72) to (81) are shown below but the compound is not limited to the following compounds.

Compound (72)

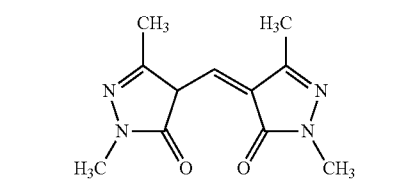

Compound (73)

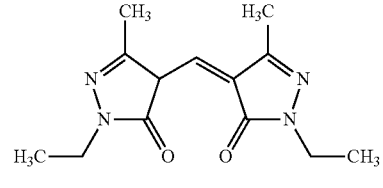

Compound (74)

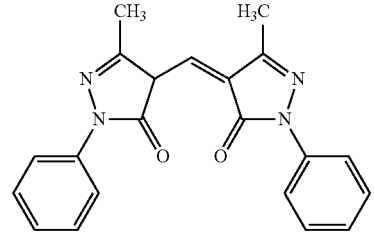

Compound (75)

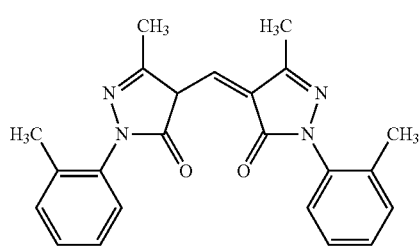

Compound (76)

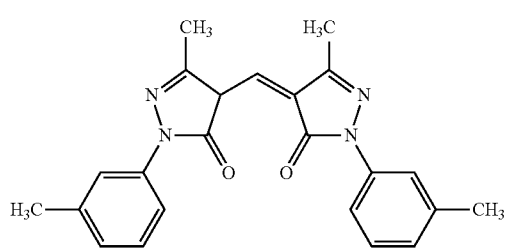

Compound (77)

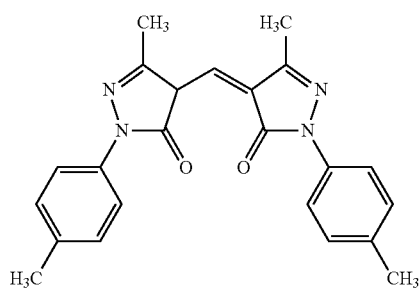

Compound (78)

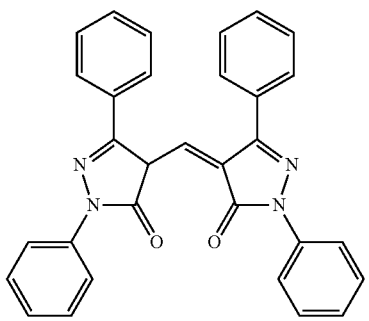

Compound (79)

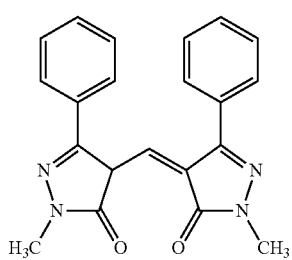

Among the above, suitable compounds are the compounds (74), (75), (76), and (77). The compound (74) is particularly suitable and the effects of the present disclosure become more remarkable in this case.

Next, the compound represented by General Formula (5) is described.

General Formula (5)

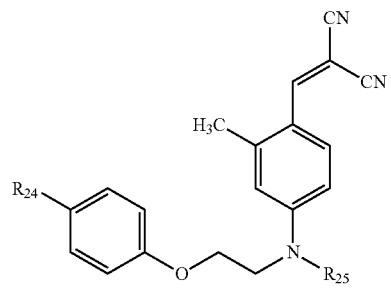

[In General Formula (5), $R_{24}$ and $R_{25}$ each independently represent an alkyl group, an unsubstituted aryl group, or an aryl group having a substituent. When $R_{24}$ and $R_{25}$ are the aryl groups having a substituent, the substituent is an alkyl group.]

In General Formula (5), the alkyl groups in $R_{24}$ and $R_{25}$ are not particularly limited and examples of the alkyl groups include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. Particularly in the case of using alkyl groups having 1 to 2 carbon atoms, such as a methyl group and an ethyl group, are used, the reproducible color gamut in the red region can be enlarged and black color with high density and low color saturation can be represented.

In General Formula (5), the aryl groups in $R_{24}$ and $R_{25}$ may be unsubstituted or may have a substituent. When $R_{24}$ and $R_{25}$ are the aryl groups having a substituent, the substituent is an alkyl group. For example, a phenyl group and a naphthyl group are mentioned. Particularly in the case of using a phenyl group, the effects of the present disclosure become more remarkable, and thus the case is suitable.

Suitable examples of the compound represented by General Formula (5), compounds (82) to (86) are shown below but the compound is not limited to the following compounds.

Compound (82)

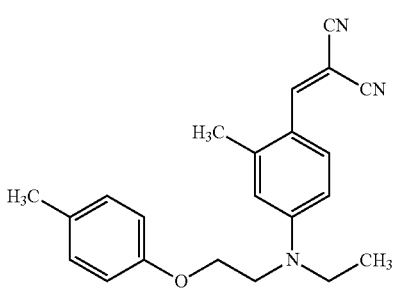

Compound (83)

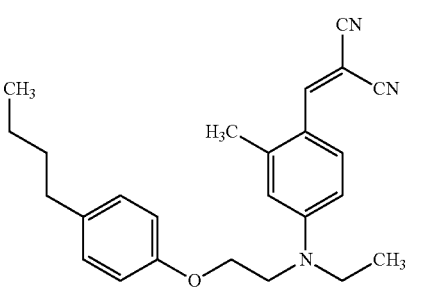

Compound (84)

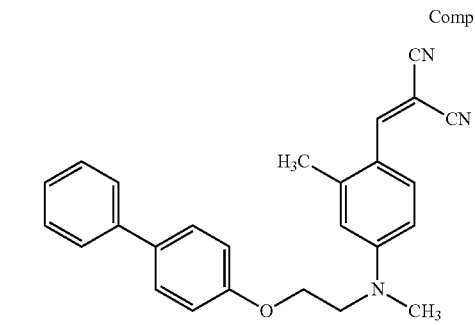

Compound (85)

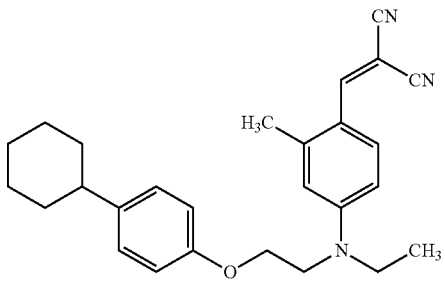

Compound (86)

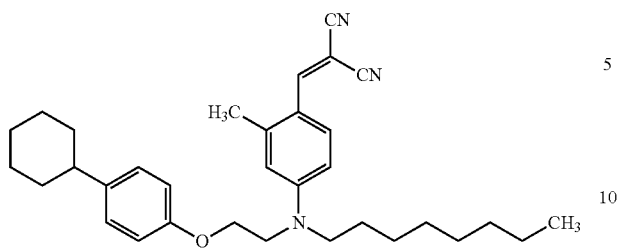

Among the above, the compounds (85) and (86) are suitable. In the case of the compound (85), the reproducible color gamut in the red region can be enlarged and black color with high density and low color saturation can be represented.

Next, the compound represented by General Formula (6) is described.

General Formula (6)

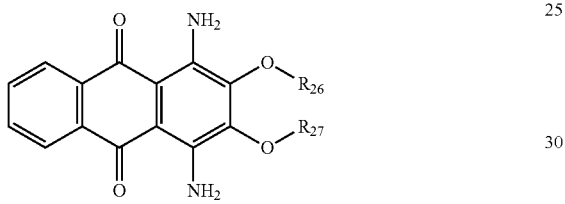

[In General Formula (6), $R_{26}$ and $R_{27}$ each independently represent an alkyl group, an unsubstituted aryl group, or an aryl group having a substituent. When $R_{26}$ and $R_{27}$ are the aryl groups having a substituent, the substituent is an alkyl group.]

In General Formula (6), the alkyl groups in $R_{26}$ and $R_{27}$ are not particularly limited and examples of the alkyl groups include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. Particularly in the case of using alkyl groups having 1 to 2 carbon atoms, such as a methyl group and an ethyl group, the reproducible color gamut in the red region can be enlarged and black color with high density and low color saturation can be represented.

In General Formula (6), the aryl groups in $R_{26}$ and $R_{27}$ may be unsubstituted or may have a substituent. When $R_{26}$ and $R_{27}$ are the aryl groups having a substituent, the substituent is an alkyl group. For example, a phenyl group and a naphthyl group are mentioned. Particularly in the case of using a phenyl group, the effects of the present disclosure become more remarkable, and thus the case is suitable.

Suitable examples of the compound represented by General Formula (6), compounds (87) to (95) are shown below but the compound is not limited to the following compounds.

Compound (87)

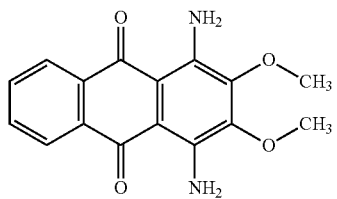

Compound (88)

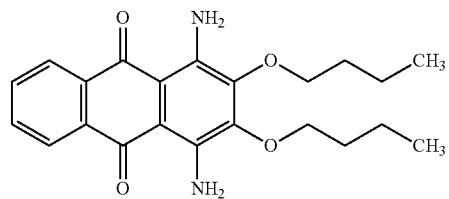

Compound (89)

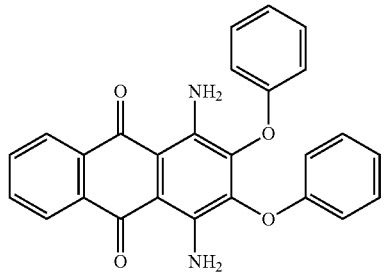

Compound (90)

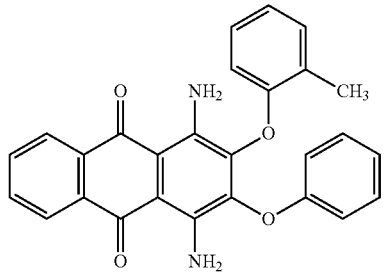

Compound (91)

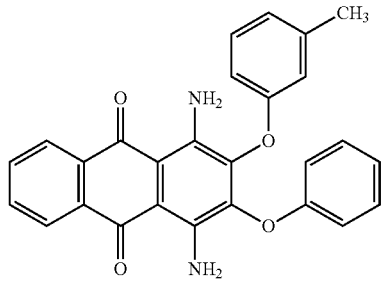

Compound (92)

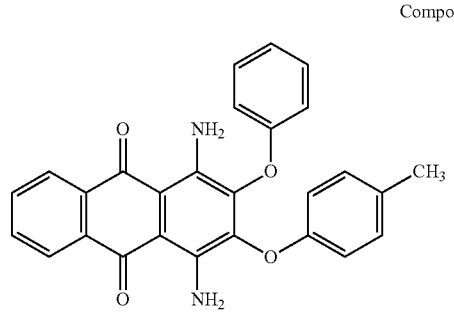

-continued

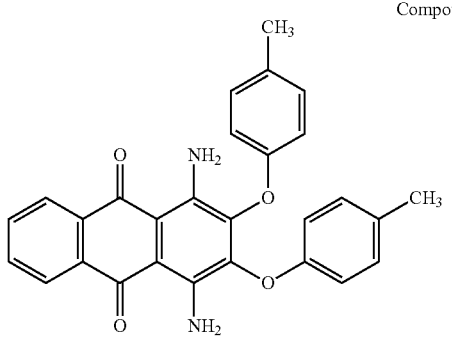
Compound (93)

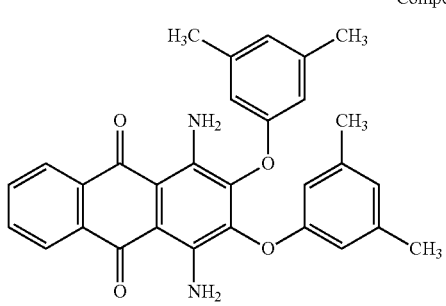
Compound (94)

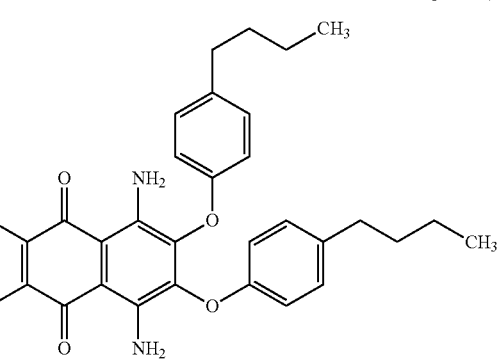
Compound (95)

Among the above, suitable compounds are the compounds (89), (90), (91), (92), (93), and (94). The compounds (89), (93), and (94) are particularly suitable. In this case, the effects of the present disclosure become more remarkable.

Next, the compound represented by General Formula (7) is described.

General Formula (7)

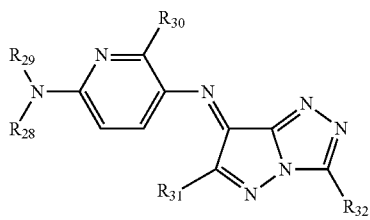

[In General Formula (7), $R_{28}$ to $R_{32}$ each independently represent an alkyl group, an unsubstituted aryl group, or an aryl group having a substituent. When $R_{28}$ to $R_{32}$ are the aryl groups having a substituent, the substituent is an alkyl group or an alkoxy group.]

In General Formula (7), the alkyl groups in $R_{28}$ to $R_{32}$ are not particularly limited and examples of the alkyl groups include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. Particularly in the case of using alkyl groups having 1 to 2 carbon atoms, such as a methyl group and an ethyl group, the reproducible color gamut in the red region can be enlarged and black color with high density and low color saturation can be represented.

In General Formula (7), the aryl groups in $R_{28}$ to $R_{32}$ may be unsubstituted or may have a substituent. When $R_{28}$ to $R_{32}$ are the aryl groups having a substituent, the substituent is an alkyl group or an alkoxy group. For example, a phenyl group and a naphthyl group are mentioned. Particularly in the case of using a phenyl group, the effects of the present disclosure become more remarkable, and thus the case is suitable.

Suitable examples of the compound represented by General Formula (7), compounds (96) to (104) are shown below but the compound is not limited to the following compounds.

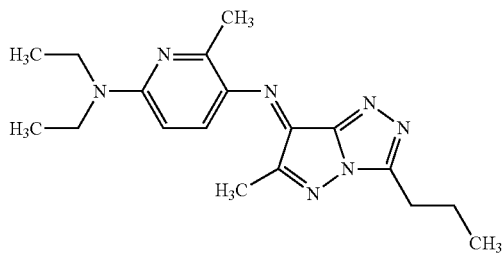
Compound (96)

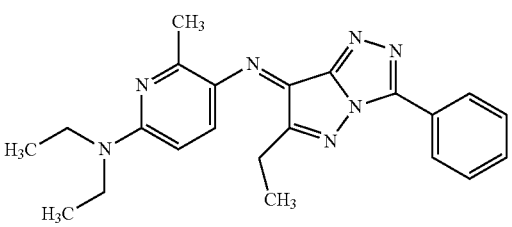
Compound (97)

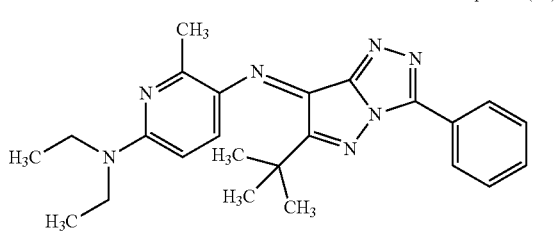
Compound (98)

Compound (99)
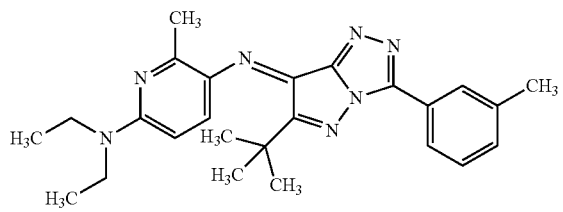

Compound (100)
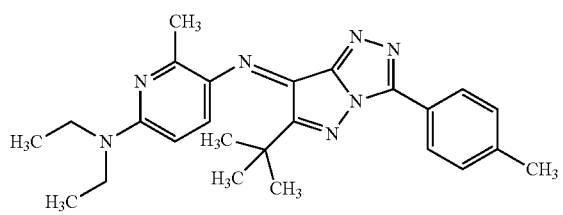

Compound (101)
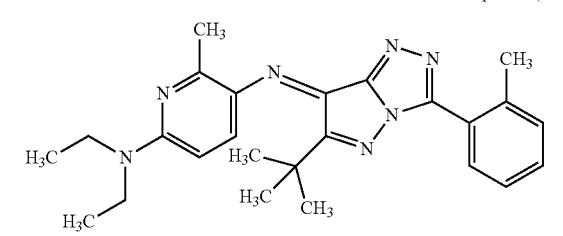

Compound (102)
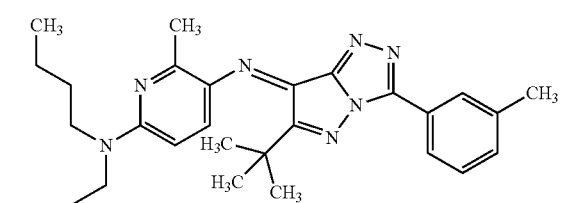

Compound (103)
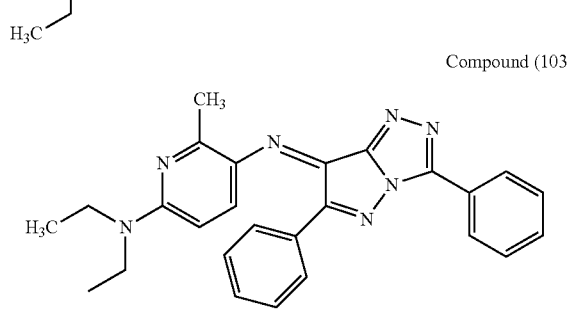

Compound (104)
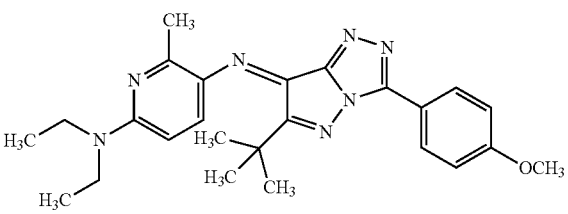

Among the above, suitable compounds are the compounds (98), (99), (100), (101), and (102). The compounds (99), (100), and (101) are particularly suitable. In this case, the effects of the present disclosure become more remarkable.

Next, the compound represented by General Formula (8) is described.

General Formula (8)
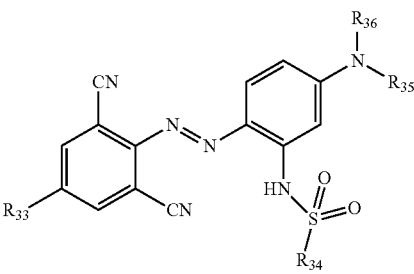

[In General Formula (8), $R_{33}$ to $R_{36}$ each independently represent an alkyl group, an unsubstituted aryl group, or an aryl group having a substituent. When $R_{33}$ to $R_{36}$ are the aryl groups having a substituent, the substituent is an alkyl group.]

In General Formula (8), the alkyl groups in $R_{33}$ and $R_{36}$ are not particularly limited and examples of the alkyl groups include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. Particularly in the case of using alkyl groups having 1 to 2 carbon atoms, such as a methyl group and an ethyl group, the reproducible color gamut in the red region can be enlarged and black color with high density and low color saturation can be represented.

In General Formula (8), the aryl groups in $R_{33}$ and $R_{36}$ may be unsubstituted or may have a substituent. When $R_{33}$ and $R_{36}$ are the aryl groups having a substituent, the substituent is an alkyl group. For example, an unsubstituted phenyl group and an unsubstituted naphthyl group are mentioned. Particularly in the case of using an unsubstituted phenyl group, the effects of the present disclosure become more remarkable, and thus the case is suitable.

Suitable examples of the compound represented by General Formula (8), compounds (105) to (113) are shown below but the compound is not limited to the following compounds.

Compound (105)
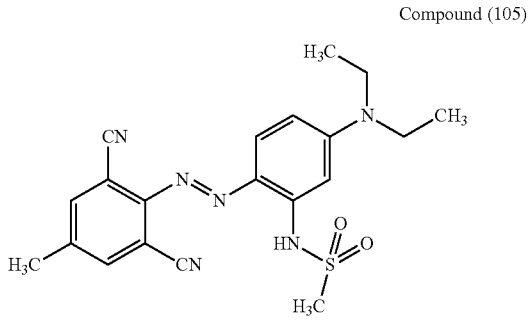

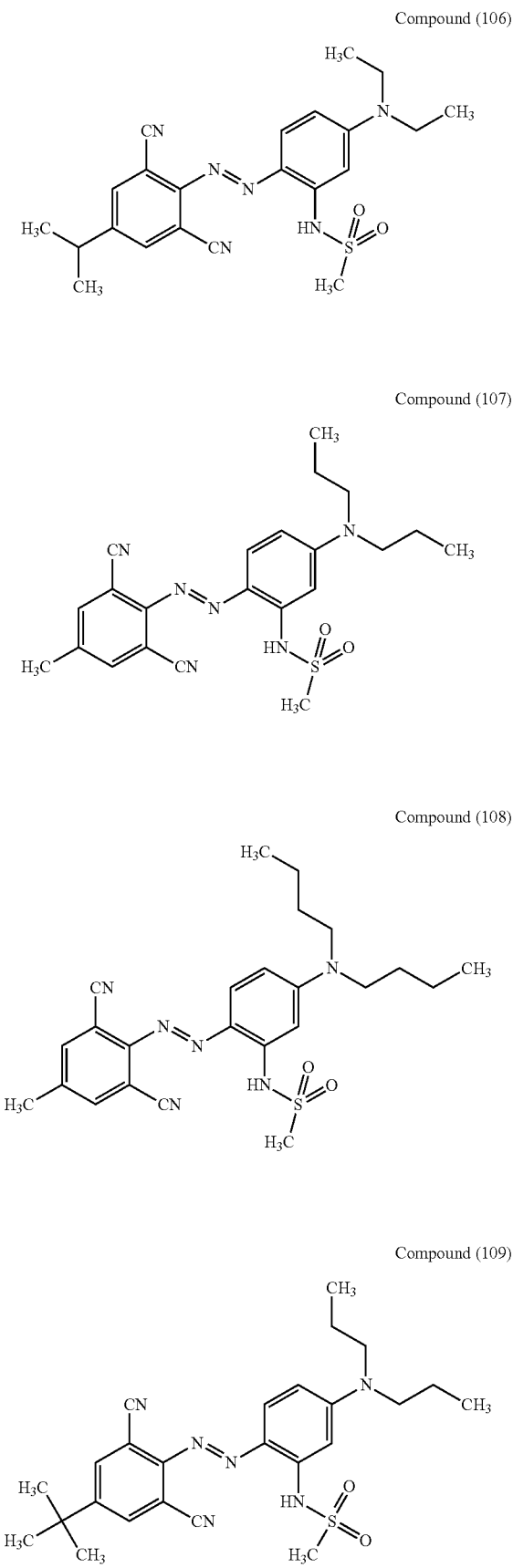
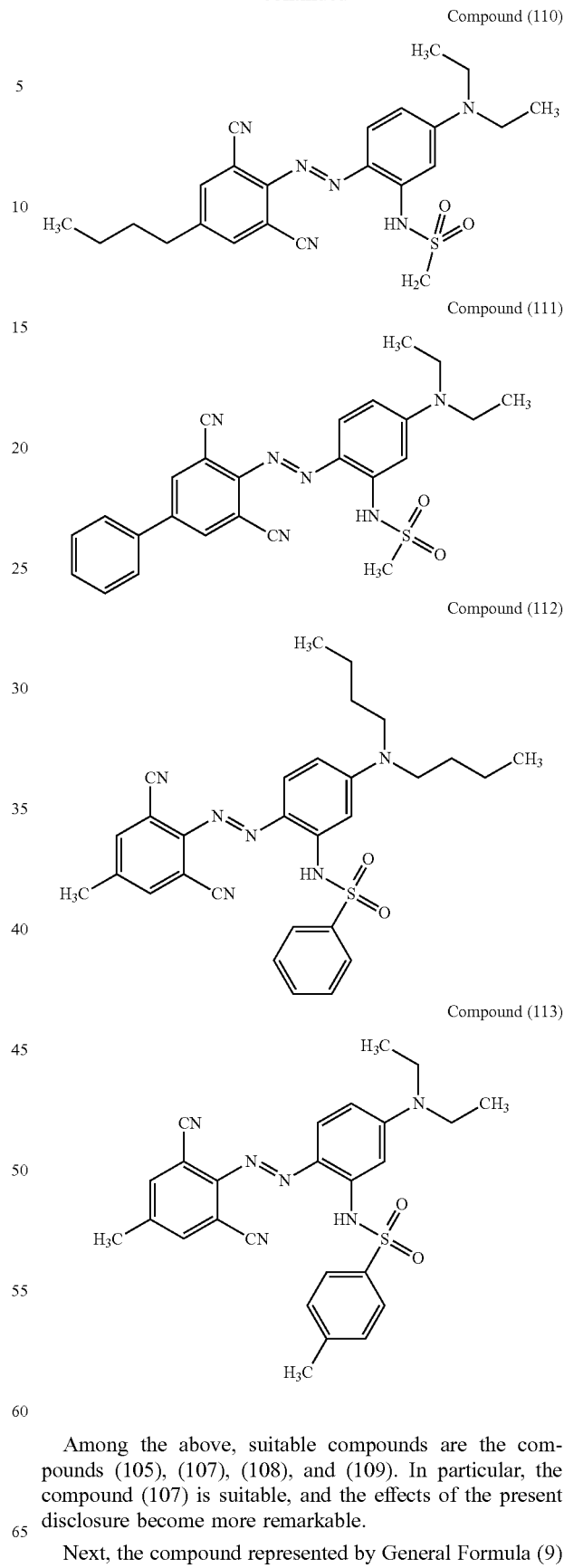
Among the above, suitable compounds are the compounds (105), (107), (108), and (109). In particular, the compound (107) is suitable, and the effects of the present disclosure become more remarkable.
Next, the compound represented by General Formula (9) is described.

General Formula (9)

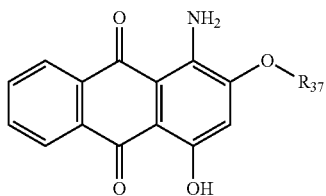

In General Formula (9), $R_{37}$ represents an alkyl group, an unsubstituted aryl group, an aryl group having a substituent, or —($R_{52}$—O)n-$R_{53}$, in which $R_{52}$ is an alkylene, $R_{53}$ is an alkyl group and n is 1 or 2. When $R_{37}$ is the aryl group having a substituent, the substituent is an alkyl group or an alkoxy group.

In General Formula (9), the alkyl group in $R_{37}$ is not particularly limited and examples of the alkyl group include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. Particularly in the case of using alkyl groups having 1 to 2 carbon atoms, such as a methyl group and an ethyl group, the reproducible color gamut in the red region can be enlarged and black color with high density and low color saturation can be represented.

In General Formula (9), the aryl group in $R_{37}$ may be unsubstituted or may have a substituent. When $R_{37}$ is the aryl group having a substituent, the substituent is an alkyl group or an alkoxy group. For example, an unsubstituted phenyl group and an unsubstituted naphthyl group are mentioned. Particularly in the case of using an unsubstituted phenyl group, the reproducible color gamut in the red region can be enlarged and black color with high density and low color saturation can be represented.

In General Formula (9), when $R_{37}$ is —($R_{52}$—O)n-$R_{53}$, $R_{52}$ is an alkylene, such as an ethylene group, $R_{53}$ is an alkyl group, such as an ethyl group, and n is 1 or 2.

Suitable examples of the compound represented by General Formula (9), compounds (114) to (122) are shown below but the compound is not limited to the following compounds.

Compound (114)

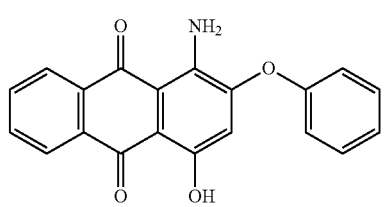

Compound (115)

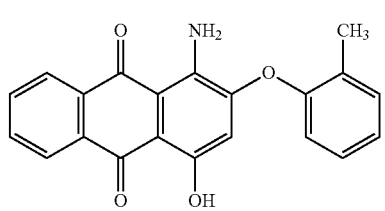

Compoiund (116)

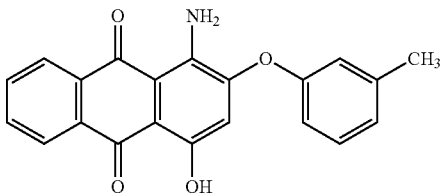

Compound (117)

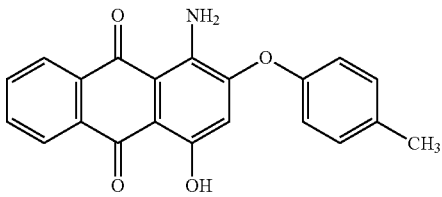

Compound (118)

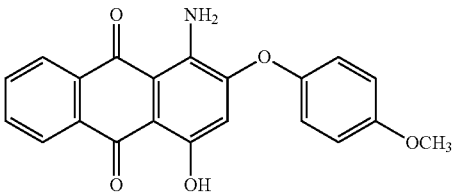

Compound (119)

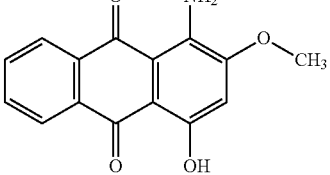

Compound (120)

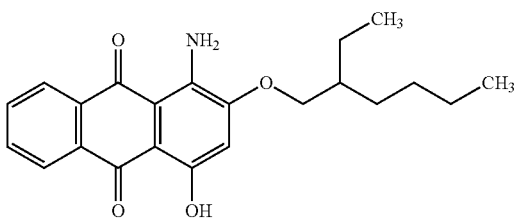

Compound (121)

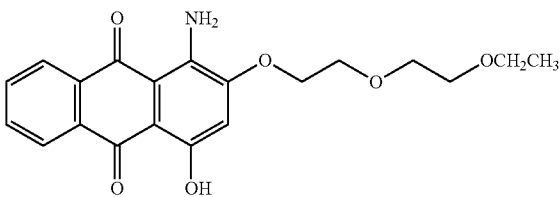

Compound (122)

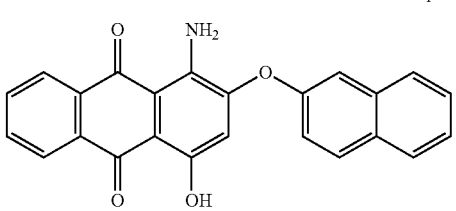

Among the above, suitable compounds are the compounds (114), (115), (116), (117), and (118). The compounds (114) and (115) are particularly suitable. In this case, the effects of the present disclosure become more remarkable.

Next, the compound represented by General Formula (10) is described.

General Formula (10)

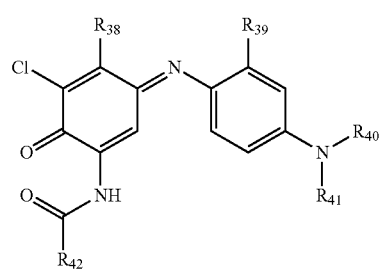

[In General Formula (10), $R_{38}$ to $R_{42}$ each independently represent an alkyl group, an unsubstituted aryl group, or an aryl group having a substituent. When $R_{38}$ to $R_{42}$ are the aryl groups having a substituent, the substituent is an alkyl group]

In General Formula (10), the alkyl groups in $R_{38}$ to $R_{42}$ are not particularly limited and examples of the alkyl groups include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. Particularly in the case of using alkyl groups having 1 to 2 carbon atoms, such as a methyl group and an ethyl group, the reproducible color gamut in the red region can be enlarged and black color with high density and low color saturation can be represented.

In General Formula (10), the aryl groups in $R_{38}$ to $R_{42}$ may be unsubstituted or may have a substituent. When $R_{38}$ and $R_{42}$ are the aryl groups having a substituent, the substituent is an alkyl group. For example, a phenyl group and a naphthyl group are mentioned. Particularly in the case of using a phenyl group, the reproducible color gamut in the red region can be enlarged and black color with high density and low color saturation can be represented.

Suitable examples of the compound represented by General Formula (10), compounds (123) to (129) are shown below but the compound is not limited to the following compounds.

Compound (123)

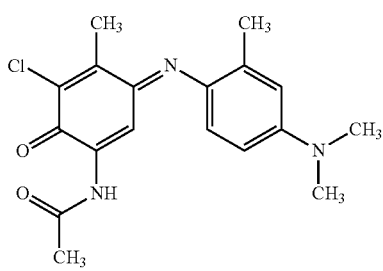

Compound (124)

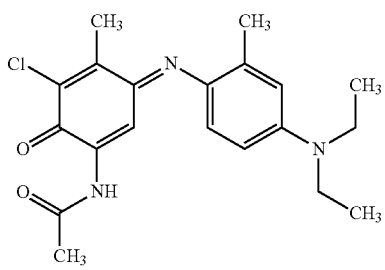

Compound (125)

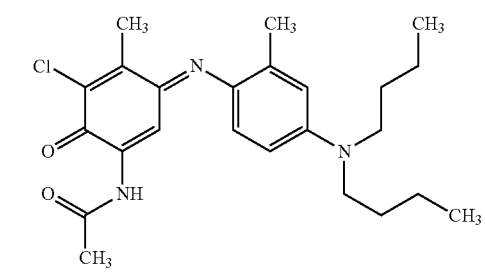

Compound (126)

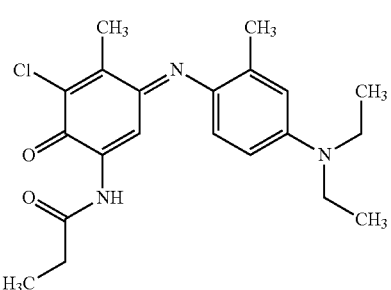

Compound (127)

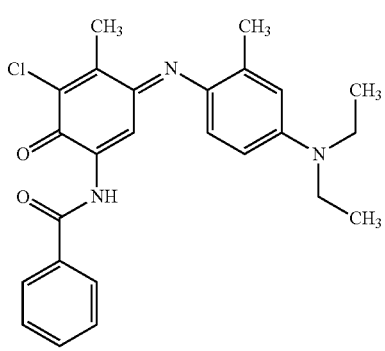

Compound (128)

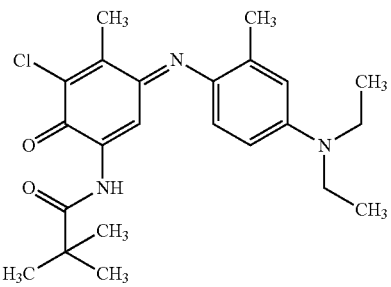

-continued

Compound (129)

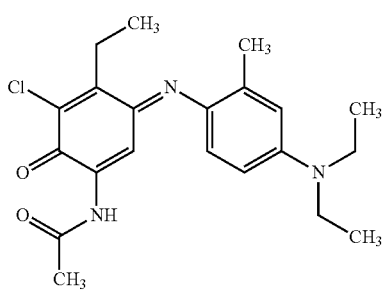

Compound (130)

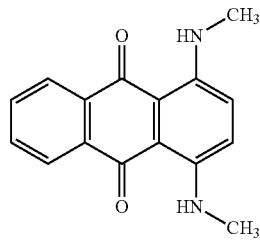

Compound (131)

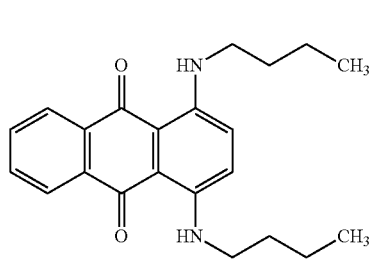

Among the above, suitable compounds are the compounds (123), (124), and (125). The compound (124) is particularly suitable. In this case, the effects of the present disclosure become more remarkable.

Next, the compound represented by General Formula (11) is described.

General Formula (11)

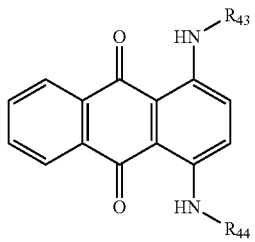

Compound (132)

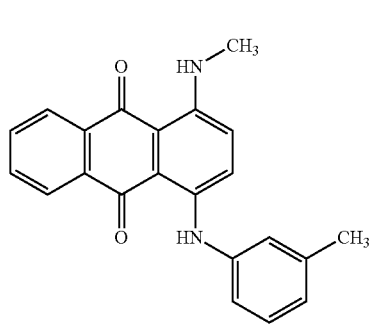

[In General Formula (11), $R_{43}$ and $R_{44}$ each independently represent an alkyl group, an unsubstituted aryl group, or an aryl group having a substituent. When $R_{43}$ and $R_{44}$ are the aryl groups having a substituent, the substituent is an alkyl group.]

In General Formula (11), the alkyl groups in $R_{43}$ and $R_{44}$ are not particularly limited and examples of the alkyl groups include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. Particularly in the case of using alkyl groups having 1 to 2 carbon atoms, such as a methyl group and an ethyl group, the reproducible color gamut in the red region can be enlarged and black color with high density and low color saturation can be represented.

In General Formula (11), the aryl groups in $R_{43}$ and $R_{44}$ may be unsubstituted or may have a substituent. When $R_{43}$ and $R_{44}$ are the aryl groups having a substituent, the substituent is an alkyl group. For example, an unsubstituted phenyl group and an unsubstituted naphthyl group are mentioned. Particularly in the case of using an unsubstituted phenyl group, the reproducible color gamut in the red region can be enlarged and black color with high density and low color saturation can be represented.

Suitable examples of the compound represented by General Formula (11), compounds (130) to (135) are shown below but the compound is not limited to the following compounds.

Compound (133)

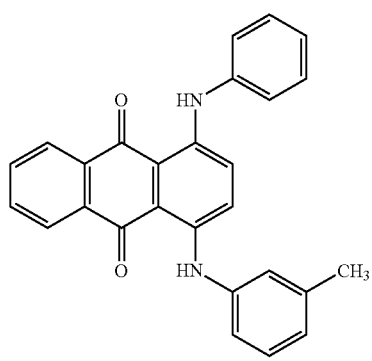

Compound (134)

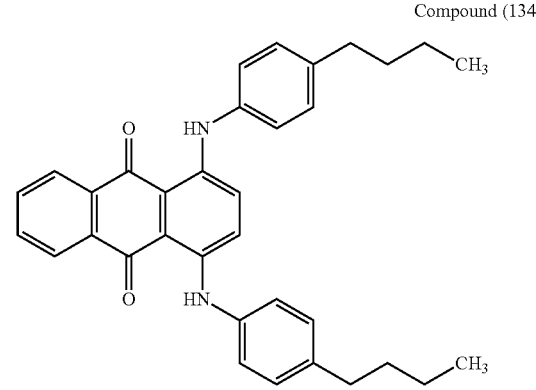

Compound (135)

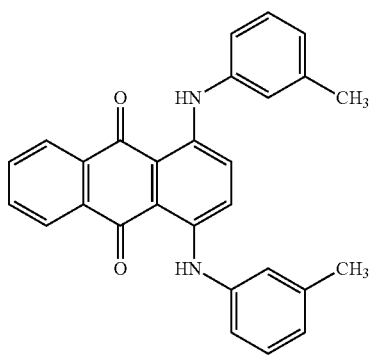

Among the above, suitable compounds are the compounds (131), (132), and (133). The compound (132) is particularly suitable. In this case, the effects of the present disclosure become more remarkable.

Next, the compound represented by General Formula (12) is described.

General Formula (12)

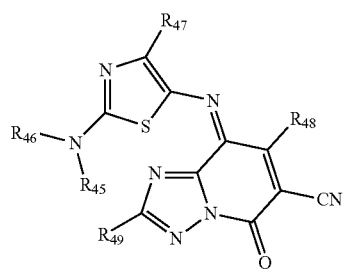

[In General Formula (12), $R_{45}$ to $R_{49}$ each independently represent an alkyl group, an unsubstituted aryl group, or an aryl group having a substituent. When $R_{45}$ to $R_{49}$ are the aryl groups having a substituent, the substituent is an alkyl group.]

In General Formula (12), the alkyl groups in $R_{45}$ to $R_{49}$ are not particularly limited and examples of the alkyl groups include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. Particularly in the case of using alkyl groups having 1 to 2 carbon atoms, such as a methyl group and an ethyl group, the reproducible color gamut in the red region can be enlarged and black color with high density and low color saturation can be represented.

In General Formula (12), the aryl groups in $R_{45}$ to $R_{49}$ may be unsubstituted or may have a substituent. When $R_{45}$ to $R_{49}$ are the aryl groups having a substituent, the substituent is an alkyl group. For example, an unsubstituted phenyl group and an unsubstituted naphthyl group are mentioned. Particularly in the case of using an unsubstituted phenyl group, the reproducible color gamut in the red region can be enlarged and black color with high density and low color saturation can be represented.

Suitable examples of the compound represented by General Formula (12), compounds (136) to (141) are shown below but the compound is not limited to the following compounds.

Compound (136)

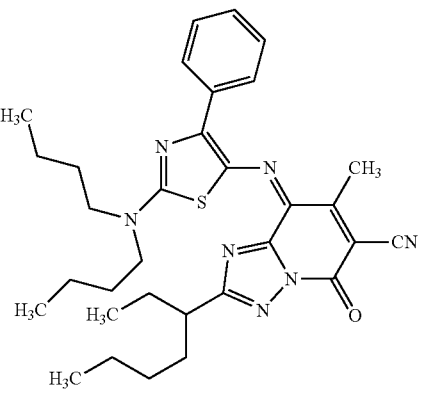

Compound (137)

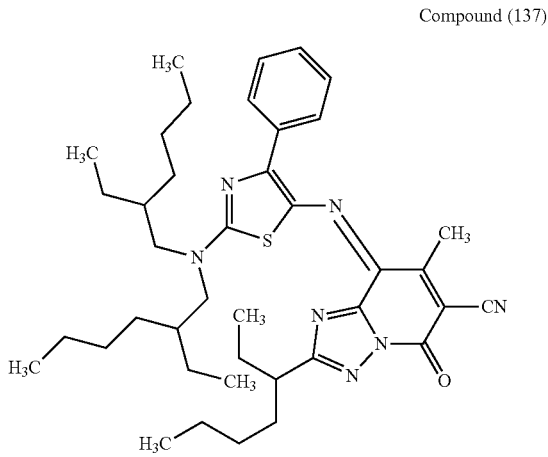

Compound (138)

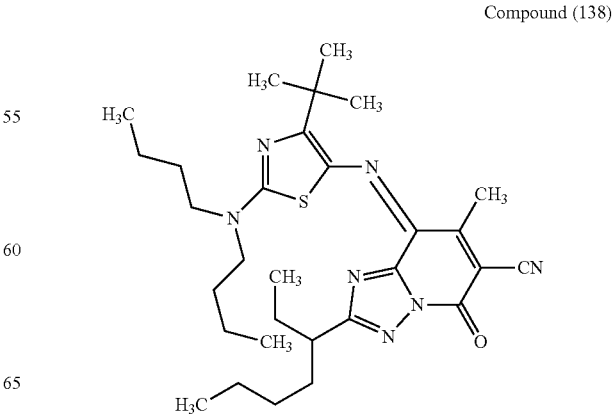

Compound (139)

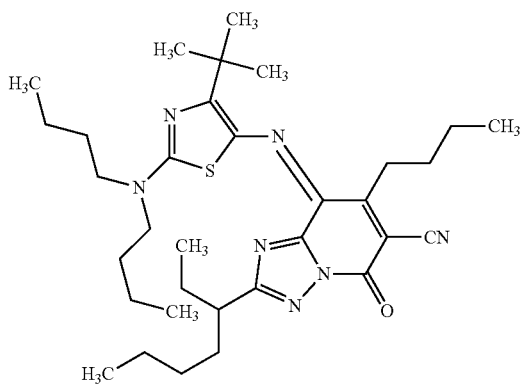

Compound (140)

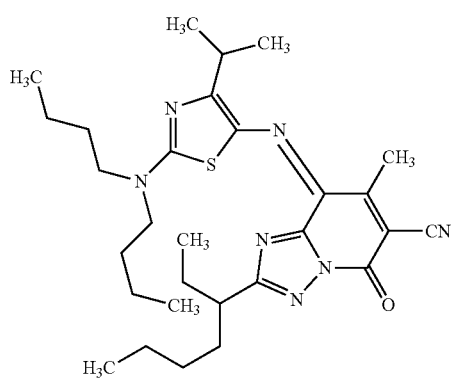

Compound (141)

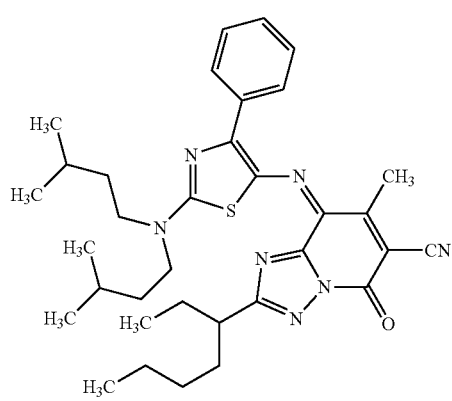

Among the above, suitable compounds are the compounds (136), (137), and (141). The compound (136) is particularly suitable. In this case, the effects of the present disclosure become more remarkable.

Next, the compound represented by General Formula (13) is described.

General Formula (13)

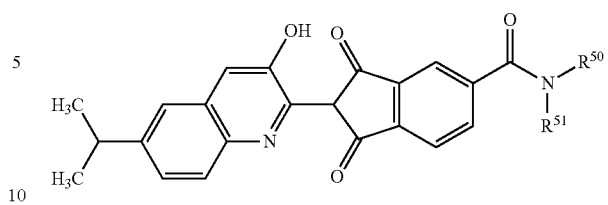

[In General Formula (13), $R_{50}$ and $R_{51}$ each independently represent an alkyl group, an unsubstituted aryl group, or an aryl group having a substituent. When $R_{50}$ and $R_{51}$ are the aryl groups having a substituent, the substituent is an alkyl group.]

In General Formula (13), the alkyl groups in $R_{50}$ and $R_{51}$ are not particularly limited and examples of the alkyl groups include, for example, saturated or unsaturated linear, branched, or cyclic primary to tertiary alkyl groups having 1 to 20 carbon atoms, such as a methyl group, an ethyl group, an n-propyl group, an iso-propyl group, an n-butyl group, a sec-butyl group, a tert-butyl group, an octyl group, a dodecyl group, a nonadecyl group, a cyclobutyl group, a cyclopentyl group, a cyclohexyl group, a methylcyclohexyl group, 2-ethylpropyl, a 2-ethylhexyl group, and a cyclohexenylethyl group. Particularly in the case of using alkyl groups having 1 to 2 carbon atoms, such as a methyl group and an ethyl group, the reproducible color gamut in the red region can be enlarged and black color with high density and low color saturation can be represented.

In General Formula (13), the aryl groups in $R_{50}$ and $R_{51}$ may be unsubstituted or may have a substituent. When $R_{50}$ and $R_{51}$ are the aryl groups having a substituent, the substituent is an alkyl group. For example, an unsubstituted phenyl group and an unsubstituted naphthyl group are mentioned. Particularly in the case of using an unsubstituted phenyl group, the reproducible color gamut in the red region can be enlarged and black color with high density and low color saturation can be represented.

Suitable examples of the compound represented by General Formula (13), compounds (141) to (149) are shown below but the compound is not limited to the following compounds.

Compound (141)

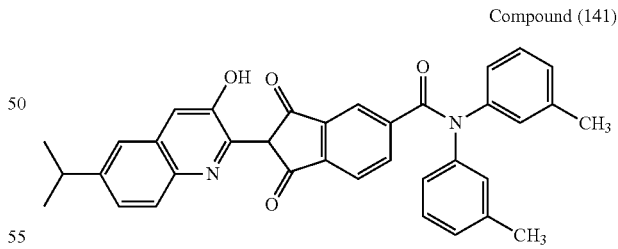

Compound (142)

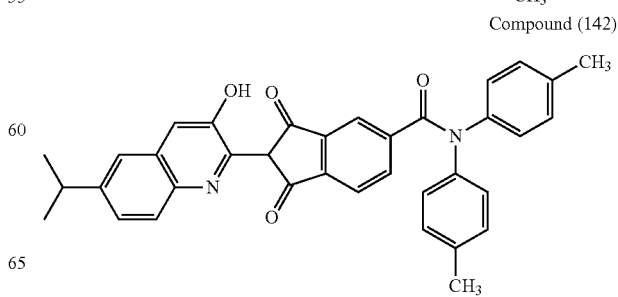

Compound (143)
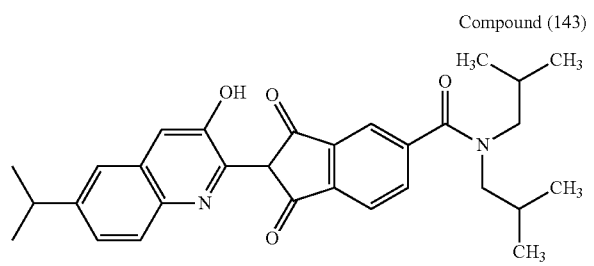

Compound (149)
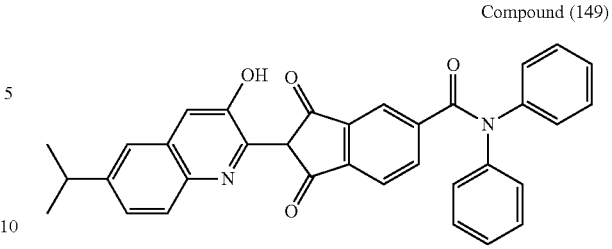

Compound (144)
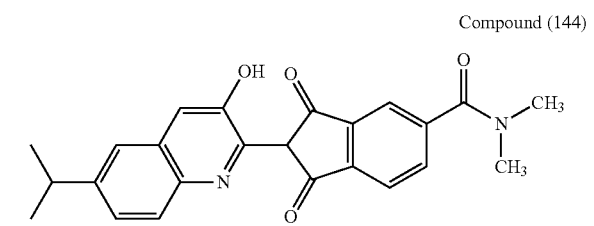

Compound (145)
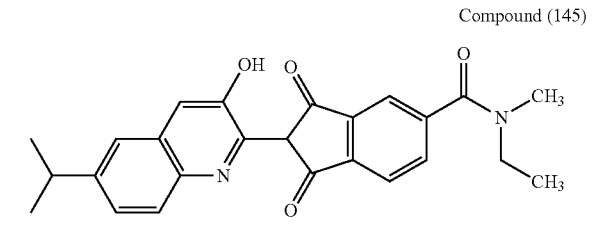

Compound (146)
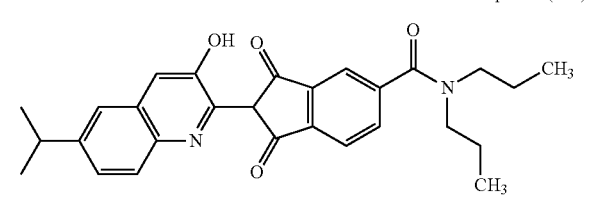

Compound (147)
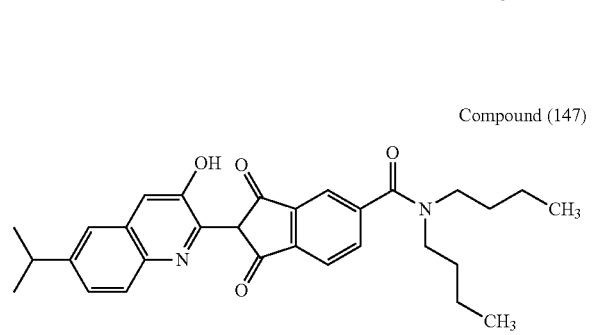

Compound (148)
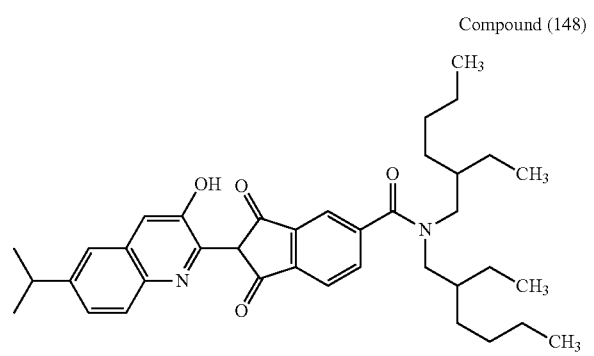

Among the above, suitable compounds are the compounds (146), (147), and (148). The compound (147) is particularly suitable. In this case, the effects of the present disclosure become more remarkable.

<Ink>

A first aspect of the present disclosure is an ink set separately having a first ink containing the compound represented by General Formula (1) above and a second ink containing the compound represented by General Formula (2) above. By the use of the ink set of the present disclosure, the reproducible color gamut in the red region can be enlarged and black color with high density and low color saturation can be represented.

For the first ink containing the compound represented by General Formula (1) and/or the second ink containing the compound represented by General Formula (2), the compounds represented by General Formulae (3) to (13) above can be selected and used as appropriate according to the purpose.

Coloring materials for use in an ink layer are not limited. The compounds represented by General Formulae (1), (3), (4), (5), and (13) are suitable as compounds for use in a yellow ink and the compounds represented by General Formulae (2), (6), (7), (8), and (9) are suitable as compounds for use in a magenta ink.

In a cyan ink to be used in combination with the inks, the compounds represented by General Formulae (10), (11), and (12) are suitably selected.

In particular, the compounds represented by General formulae (1), (3), and (5) are suitably selected as the compounds for use in a yellow ink, the compounds represented by General Formula (2), (7), and (9) are suitably selected as the compounds for use in a magenta ink, and the compounds represented by General Formula (10) and (11) are suitably selected as the compounds for use in a cyan ink.

It is a matter of course that known dyes already known as a thermal transfer coloring material may be added for use.

On the other hand, the ink set may be produced by adding a process black ink whose color is adjusted by combining the compounds of General Formulae (1) to (13) as appropriate or a known black ink.

The ink of the present disclosure is obtained as follows.

The compounds of the present disclosure are gradually added to a medium under stirring, as necessary, together with another coloring agent, an emulsifier, and a resin, so as to be sufficiently mixed with the medium. Then, the mixture is stably dissolved or dispersed by applying mechanical shearing force with a disperser, and thus, the ink of the present disclosure can be obtained.

The "medium" means water or an organic solvent.

When an organic solvent is used as the medium of the ink, the type of the organic solvent is not particularly limited and is determined according to the purpose and the application of the coloring agent. Specific examples of the organic solvent include alcohols, such as methanol, ethanol, denatured ethanol, isopropanol, n-butanol, isobutanol, tert-butanol, sec-butanol, 2-methyl-2-butanol, 3-pentanol, octanol, benzyl alcohol, and cyclohexanol, glycols, such as methyl cellosolve, ethyl cellosolve, diethylene glycol, and diethylene glycol monobutyl ether, ketones, such as acetone, methyl ethyl ketone, and methyl isobutyl ketone, esters, such as ethyl acetate, butyl acetate, ethyl propionate, and cellosolve acetate, aliphatic hydrocarbons, such as hexane, octane, petroleum ether, and cyclohexane, aromatic hydrocarbons such as benzene, toluene, and xylene, halogenated hydrocarbons, such as carbon tetrachloride, trichloroethylene, and tetrabromoethane, ethers, such as diethyl ether, dimethyl glycol, trioxane, and tetrahydrofuran, acetals, such as methylal and diethyl acetal, organic acids, such as formic acid, acetic acid and propionic acid, and sulfur- or nitrogen-containing organic compounds such as nitrobenzene, dimethyl amine, monoethanol amine, pyridine, dimethyl sulfoxide, and dimethylformamide.

As the organic solvent usable in the ink of the present disclosure, a polymerizable monomer can also be used. The polymerizable monomer is an addition polymerizable monomer or a condensation polymerizable monomer and is suitably an addition polymerizable monomer. Examples of such polymerizable monomers include, styrene monomers, such as styrene, α-methylstyrene, α-ethylstyrene, o-methylstyrene, m-methylstyrene, p-methylstyrene, o-ethylstyrene, m-ethylstyrene and p-ethylstyrene, acrylate monomers, such as methyl acrylate, ethyl acrylate, propyl acrylate, butyl acrylate, octyl acrylate, dodecyl acrylate, stearyl acrylate, behenyl acrylate, 2-ethylhexyl acrylate, dimethylaminoethyl acrylate, diethylaminoethyl acrylate, acrylonitrile and acrylic acid amide, methacrylate monomers, such as methyl methacrylate, ethyl methacrylate, propyl methacrylate, butyl methacrylate, octyl methacrylate, dodecyl methacrylate, stearyl methacrylate, behenyl methacrylate, 2-ethylhexyl methacrylate, dimethylaminoethyl methacrylate, diethylaminoethyl methacrylate, methacrylonitrile and methacrylic acid amide, olefin monomers, such as ethylene, propylene, butylene, butadiene, isoprene, isobutylene and cyclohexane, halogenated vinyl monomers, such as vinyl chloride, vinylidene chloride, vinyl bromide and vinyl iodide, vinyl ester monomers, such as vinyl acetate, vinyl propionate and vinyl benzoate, vinyl ether monomers, such as vinyl methyl ether, vinyl ethyl ether and vinyl isobutyl ether, and vinyl ketone monomers, such as vinyl methyl ketone, vinyl hexyl ketone and methyl isopropenyl ketone. The substances can be used alone or in combination of two or more kinds thereof.

As the coloring agent forming the ink of the present disclosure, the compound represented by General Formula (1) or (2) is used and another coloring agent may be used in combination as necessary insofar as the solubility or the dispersibility of the compound in the medium is not impeded.

Examples of the other coloring agents usable in combination include, but are not limited thereto, a condensed azo compound, an azo metal complex, a metin compound, and the like.

The content of the coloring agent contained in the ink of the present disclosure is preferably 1.0 to 30.0 parts by mass, more preferably 2.0 to 20.0 parts by mass, and still more preferably 3.0 to 15.0 parts by mass based on 100.0 parts by mass of the medium. In the case of the ranges mentioned above, sufficient tinting strength is obtained and the dispersibility of the coloring agent is improved.

When water is used as the medium of the ink of the present disclosure, an emulsifier may be added as necessary for obtaining good dispersion stability of the coloring agent. Emulsifiers that can be added are not particularly limited, and a cationic surfactant, an anionic surfactant, and a nonionic surfactant are mentioned.

Examples of the cationic surfactant include dodecyl ammonium chloride, dodecyl ammonium bromide, dodecyl trimethyl ammonium bromide, dodecyl pyridinium chloride, dodecyl pyridinium bromide, and hexadecyl trimethyl ammonium bromide.

Examples of the anionic surfactant include fatty acid soap, such as a formalin condensate of aromatic sulfonic acid, sodium stearate, and sodium dodecanoate, sodium dodecyl sulfate, sodium dodecylbenzene sulfate, and sodium lauryl sulfate.

Examples of the nonionic surfactant include dodecyl polyoxyethylene ether, hexadecyl polyoxyethylene ether, nonylphenyl polyoxyethylene ether, lauryl polyoxyethylene ether, sorbitan monoleate polyoxyethylene ether, and monodecanoyl sucrose.

The ink may further contain a resin. The type of the resin that can be contained in the ink of the present disclosure is not particularly limited but can be determined according to the purpose and the application. Examples of the resin include a polystyrene resin, a styrene copolymer, a polyacrylic acid resin, a polymethacrylic acid resin, a polyacrylate resin, a polymethacrylate resin, an acrylic acid copolymer, a methacrylic acid copolymer, a polyester resin, a polyvinyl ether resin, a polyvinyl methyl ether resin, a polyvinyl alcohol resin, a polyvinyl butyral resin, a polyurethane resin, and a polypeptide resin. These resins may be used alone or in combination of two or more kinds thereof.

The disperser is not particularly limited, and a media type disperser, such as a rotary shearing homogenizer, a ball mill, a sand mill, or an attritor, or a high-pressure counter collision disperser can be used.

The ink set of the present disclosure may be applied to any device without causing any problem insofar as the device forms an image. For example, image forming devices employing an ink jet system and an electrophotographic system can be mentioned.

The effects of the present disclosure are obtained by forming an image on a fabric using the ink set of the present disclosure by a known method. In particular, the effects of the present disclosure are more notably obtained when the first ink and the second ink of the present disclosure are placed in the same ink-jet printer, an image is formed on an intermediate transfer body, the surface to which the inks are given and the dyeing surface of a dyeing target are heated in a state where the surfaces are made to face each other, and then the image is formed on the fabric by a method of transferring the image to the surface to be dyed.

The fabric which can be subjected to printing is not particularly limited insofar as the fabric is dyed. For example, fibers containing polyester, acetate, and triacetate may be used in any form of a woven stuff, a knitted stuff, or a nonwoven stuff. Fabrics containing cotton, silk, hemp, polyurethane, acryl, nylon, wool, and rayon fibers, or fabrics containing a mixture of two or more kinds of these fibers are mentioned.

<Thermal Transfer Recording Sheet>

A second aspect of the present disclosure is a thermal transfer recording sheet having a first coloring material layer containing the compound represented by General Formula (1) above and a second coloring material layer containing the compound represented by General Formula (2) above.

The thermal transfer recording sheet is a sheet used for forming an image on a recording medium by heating the thermal transfer recording sheet by a heating unit to sublimate the coloring materials present in the coloring material layers to move the same to the recording medium. As the heating unit, a thermal head is generally used but infrared rays or laser beams can also be utilized. Alternatively, heat can be generated by passing electricity through a substrate of the thermal transfer recording sheet.

By providing the first coloring material layer and the second coloring material layer, a thermal transfer recording sheet having both red color reproducibility and black color reproducibility can be obtained. More specifically, the reproducible color gamut in the red region can be enlarged and black color with high density and low color saturation can be represented.

In order to obtain a full color image, it is necessary to form a thermal transfer sheet at least containing a yellow layer, a magenta layer, and a cyan layer. The first coloring material layer and the second coloring material layer of the present disclosure may be some of these layers.

In at least either the first coloring material layer containing the compound represented by General Formula (1) or the second coloring material layer containing the compound represented by General Formula (2), the compounds represented by General Formulae (3) to (13) above can be blended.

The coloring material for use in the coloring material layers is not limited. Compounds for use in the yellow layer are suitably the compounds represented by General Formulae (1), (3), (4), (5), and (13). Compounds for use in the magenta layer are suitably the compounds represented by General Formulae (2), (6), (7), (8), and (9). Compounds for use in the cyan layer to be used in combination with these layers are suitably the compounds represented by General Formula (10), (11), and (12).

In particular, the compounds represented by General Formulae (1), (3), and (5) are suitably selected as the compounds for use in the yellow layer. The compounds represented by General Formulae (2), (7), and (9) are suitably selected as the compounds for use in the magenta layer. The compounds represented by General Formulae (10) and (11) are suitably selected as the compounds for use in the cyan layer.

Moreover, known dyes already known as the thermal transfer coloring material may be further added for use.

Hereinafter, each layer configuring the thermal transfer recording sheet of the present disclosure is described.

<Substrate>

A substrate configuring the thermal transfer recording sheet supports ink layers described later and known substrates can be used. Known substrates may be used without particular limitation insofar as the substrates have a certain degree of heat resistance and strength. For example, a polyethylene terephthalate film, a polyethylenenaphthalate film, a polycarbonate film, a polyimide film, a polyamide film, an aramid film, a polystyrene film, a 1,4-polycyclohexylenedimethylene terephthalate film, a polysulphone film, a polypropylene film, a polyphenylene sulfide film, a polyvinyl alcohol film, cellophane, a cellulose derivative, a polyethylene film, a polyvinylchloride film, a nylon film, a condenser paper, and a wax paper are mentioned.

In particular, a polyethylene terephthalate film is more suitable in the respects of mechanical strength, solvent resistance, and economical efficiency.

The thickness of the substrate is 0.5 to 50 µm and preferably 3 to 10 µm in terms of transferability.

The substrate is suitably subjected to adhesion processing on one surface or both surfaces as necessary. When a dye ink is applied in order to form a dye layer on the substrate, it is usually suitable to perform the adhesion processing because the wettability, adhesiveness, and the like of a coating liquid are likely to be insufficient.

The adhesion processing is not particularly limited and, for example, ozone treatment, corona discharge treatment, ultraviolet ray treatment, plasma treatment, low-temperature plasma treatment, primer treatment, chemical treatment, and the like can be mentioned, for example. Two or more kinds of the treatment above may be combined.

For the adhesion processing of the substrate, an adhesive layer may be applied onto the substrate.

The adhesive layer is not particularly limited and, for example, organic materials, such as polyester resin, polystyrene resin, polyacrylic ester resin, polyamide resin, polyether resin, polyvinyl acetate resin, polyethylene resin, polypropylene resin, polyvinyl chloride resin, polyvinyl alcohol resin, and polyvinyl butyral resin, inorganic fine particles, such as silica, alumina, magnesium carbonate, magnesium oxide, and titanium oxide are mentioned.

<Coloring Material Layer>

In the thermal transfer recording sheet of the present disclosure, at least a yellow layer, a magenta layer, and a cyan layer as coloring material layers are formed on the substrate. In the thermal transfer recording sheet, a known former black layer may be added as the coloring material layer.

In the thermal transfer recording sheet of the present disclosure, each ink layer is configured in a plane sequential manner (state in which the layers are not laminated but are horizontally disposed side by side) on the substrate but the configuration is not particularly limited thereto. For example, a plurality of ink layers of yellow, magenta, cyan, black, and the like are repeatedly configured in a plane sequential manner in the form of a substrate sheet. Furthermore, in addition to the plurality of ink layers, a transferable protective layer can be added in a plane sequential manner. Moreover, a heat-melting black may be added.

A method for forming the thermal transfer recording sheet of the present disclosure is not particularly limited and the thermal transfer recording sheet can be obtained as follows.

A coloring agent containing the specific compounds described above, a binder resin, and a surfactant and, as necessary, a wax are gradually added into a medium under stirring, so as to be sufficiently mixed with the medium. Furthermore, the composition is stably dissolved or finely dispersed by applying mechanical shearing force with a disperser, and thus, an ink of the present disclosure is prepared. Next, the ink is applied onto a base film serving as the substrate and then dried to form coloring material layers, and thus, the thermal transfer recording sheet of the present disclosure can be prepared. The thermal transfer recording sheet of the present disclosure is not limited to a thermal transfer recording sheet produced by the production method.

The medium usable in the production method described above are not particularly limited and, for example, water or an organic solvent is mentioned. As the organic solvent, alcohols, such as methanol, ethanol, isopropanol, and isobutanol, cellosolves, such as methyl cellosolve and ethyl cellosolve, aromatic hydrocarbons, such as toluene, xylene, and chlorobenzene, esters, such as ethyl acetate and butyl acetate, ketones, such as acetone, methyl ethyl ketone, methyl isobutyl ketone, and cyclohexanone, halogenated hydrocarbons, such as methylene chloride, chloroform, and trichloroethylene, ethers, such as tetrahydrofuran and dioxane, N,N-dimethylformamide, and N-methyl pyrrolidone are suitably used. These organic solvents may be used alone or in combination of two or more kinds thereof as necessary.

The use amount of the coloring material for use in the formation of the coloring material layer is 50 to 300 parts by mass, preferably 80 to 280 parts by mass, and more preferably 85 to 250 parts by mass based on 100 parts by mass of the binder resin. The use amount above is the total amount of the compounds when a mixture of two or more kinds of the compounds of the present disclosure and known compounds, such as pigments, is used.

As the binder resin usable in the thermal transfer recording sheet, various kinds of resin are mentioned. In particular, water soluble resin, such as a cellulose resin, a polyacrylic acid resin, a starch resin, and an epoxy resin, and organic solvent soluble resin, such as a polyacrylate resin, a polymethacrylate resin, a polystyrene resin, a polycarbonate resin, a polyether sulfone resin, a polyvinyl butyral resin, an ethyl cellulose resin, an acetyl cellulose resin, a polyester resin, an AS resin, and a phenoxy resin, are suitable. The various kinds of resin may be used alone or in combination of two or more of kinds thereof.

To the thermal transfer recording sheet of the present disclosure, a surfactant may be added in order to give sufficient lubricity in heating with a thermal head (in image printing). Examples of the surfactants which can be added thereto include cationic surfactants, anionic surfactants, and nonionic surfactants.

Examples of the cationic surfactants include dodecyl ammonium chloride, dodecyl ammonium bromide, dodecyl trimethyl ammonium bromide, dodecyl pyridinium chloride, dodecyl pyridinium bromide, and hexadecyl trimethyl ammonium bromide.

Examples of the anionic surfactants include fatty acid soap, such as sodium stearate and sodium dodecanoate, sodium dodecyl sulfate, sodium dodecylbenzene sulfate, and sodium lauryl sulfate.

Examples of the nonionic surfactants include dodecyl polyoxyethylene ether, hexadecyl polyoxyethylene ether, nonylphenyl polyoxyethylene ether, lauryl polyoxyethylene ether, sorbitan monooleate polyoxyethylene ether, and monodecanoyl sucrose.

To the thermal transfer recording sheet of the present disclosure, a wax may be added in order to give sufficient lubricity when not heated with a thermal head. Examples of the wax that can be added include, but are not limited thereto, a polyethylene wax, a paraffin wax, and a fatty acid ester wax.

To the thermal transfer recording sheet of the present disclosure, a UV absorber, an antiseptic agent, an antioxidant, an antistatic agent, and a viscosity modifier may be added as necessary in addition to the aforementioned additives.

In the thermal transfer recording sheet of the present disclosure, layers of a lubricant, heat-resistant fine particles with high lubricity, and a thermal resin, such as a binding agent, are suitably provided on a surface opposite to the surface on which the coloring material layers are provided of the substrate for the purpose of improving the heat resistance and the travelling performance of the thermal head. Examples of the lubricant include an amino-modified silicone compound and a carboxy-modified silicone compound. Examples of the heat-resistant fine particles include fine particles, such as silica. Examples of the binding agent include an acrylic resin. These examples, however, do not limit the substances above.

A method for applying the ink onto the substrate is not particularly limited, and methods employing a bar coater, a gravure coater, a reverse roll coater, a rod coater, and an air doctor coater are mentioned. A gravure coater is particularly suitable.

In the application, the drying may be performed for about 1 second to about 5 minutes at a temperature of 50 to 120° C. but is not particularly limited thereto. When the drying is insufficient, scumming or offset of ink in winding occurs in some cases.

As the application amount of the ink, it is suitable to apply the ink in such a manner that the thickness after drying of the coloring material layers is in the range of 0.1 to 5 μm in terms of transferability.

[Other Layers]

In the thermal transfer recording sheet of the present disclosure, a transfer protective layer which protects an image surface after image formation may be formed in a plane sequential manner with the coloring material layers described above.

The thermal transfer recording sheet of the present disclosure may have a heat-resistant lubricant layer for preventing sticking, wrinkles of a printed image, and the like on the substrate surface opposite to the surface on which the dye layers described above are to be formed.

The heat-resistant lubricant layer is formed from a heat-resistant resin. The heat-resistant resin is not particularly limited and, for example, polyvinyl butyral resin, polyvinyl acetal resin, polyester resin, polyether resin, polybutadiene resin, vinyl chloride-vinyl acetate copolymer resin, styrene-butadiene copolymer resin, polyurethane acrylate, polyester acrylate, polyimide resin, and polycarbonate resin are mentioned.

To the heat-resistant lubricant layer, a crosslinking agent, a mold release agent, a slipperiness imparting agent, and the like may be further added.

As the heat-resistant lubricant layer, the resin and the additives mentioned above are added to a solvent, and then dissolved or dispersed to produce a heat-resistant lubricant layer coating liquid. Then, the heat-resistant lubricant layer coating liquid is applied. A method for applying the heat-resistant lubricant layer coating liquid is not particularly limited, and methods employing a bar coater, a gravure coater, a reverse roll coater, a rod coater, and an air doctor coater are mentioned. A gravure coater is particularly suitable. As the application amount of the heat-resistant lubricant layer coating liquid, it is suitable to apply the heat-resistant lubricant layer coating liquid in such a manner that the thickness after drying of the coloring material layers is in the range of 0.1 to 5 μm in terms of transferability.

EXAMPLES

Hereinafter, the present disclosure is described in more detail with reference to Examples and Comparative Examples but the present disclosure is not limited to these examples. In the following description, the terms "part(s)" and "%" are based on mass unless otherwise particularly specified. The obtained compounds were identified using a $^1$H nuclear magnetic resonance ($^1$H-NMR) spectrometer (ECA-400, manufactured by JEOL Ltd.) and an LC/TOF MS (LC/MSD TOF, manufactured by Agilent Technologies Inc.).

Production Example 1

Production of Compound (1)

Into 25 mL of ethanol suspension of 12 mmol of ethylacetoacetate, 12 mmol of phenylhydrazine was added, the temperature was increased to 80° C., and then heating and refluxing were carried out for 3 hours. Next, 11 mmol of aldehyde compound (1) and 13 mmol of ammonium acetate were added, the temperature was increased to 80° C., and then heating and refluxing were carried out for 3 hours. After the completion of a reaction, the temperature was reduced to room temperature, and then the resultant substance was condensed under reduced pressure. 50 mL of ethyl acetate and 50 mL of water were added, the mixture was neutralized in a saturated sodium hydrogencarbonate aqueous solution, and then liquid separation was carried out. The organic layer was concentrated under reduced pressure, the residue was purified by column chromatography (Developing solvent: Ethylacetate/Hexane), and thus the compound (1) (19.3% yield) was obtained.

[Analysis Results of Compound (1)]

[1] $^1$H-NMR (400-MHz, CDCl$_3$, room temperature): δ (ppm)=0.97 (6H) dd, J=5.3 or 12.6 Hz, 0.94-0.99 (4H, m), 1.53 (9H, s), 1.64-1.71 (4H, m), 2.28 (3H, s), 3.56 (4H, br), 7.12 (1H, t, J=7.3 Hz), 7.38 (2H, dd, J=5.3 or 10.8 Hz), 7.98 (3H, dd, J=8.7 or 9.6 Hz).

[2] Mass spectrometry (ESI-TOF): m/z=453.2820 (M+H)$^+$

Other compounds of General Formula (1) in Table 1 were produced by the same method as that of Production Example 1 and then were identified by the same method as that of Production Example 1.

Y, M, and C in each table represent yellow, magenta, and cyan, respectively.

Production of Thermal Transfer Recording Sheet

Production Example 1

Into a mixed solution of 45 parts of methylethylketone/45 parts of toluene, 5 parts of polyvinyl butyral resin (Denka 3000-K; manufactured by Sekisui Chemical Co., Ltd.) was gradually added to be dissolved. In the solution, 5 parts of the compound (1) was completely dissolved, whereby an ink for producing a thermal transfer recording sheet (1) was obtained.

The ink for producing a thermal transfer recording sheet (1) was applied to a 4.5 μm thick polyethylene terephthalate film (Lumirror; manufactured by Toray Industries, Inc.) in such a manner that the thickness after drying was 1 μm, and then dried, whereby a thermal transfer recording sheet (Y1) was produced.

Production Examples 2 to 16

Thermal transfer recording sheets (Y2) to (Y16) were obtained in the same manner as in Production Example 1, except using compounds of the "compounding ratio" of General Formulae (1), (3) to (5), and (13) shown in Table 1 in place of using the compound (1) in Production Example 1.

TABLE 1

| Thermal transfer recording sheet | General Formula (1) | General Formula (3) | General Formula (4) | General Formula (5) | General Formula (13) | Compounding ratio |
|---|---|---|---|---|---|---|
| Y1 | Compound (1) | — | — | — | — | 1:0:0:0:0 |
| Y2 | Compound (3) | Compound (67) | Compound (74) | — | — | 1:1:1:0:0 |
| Y3 | Compound (6) | Compound (68) | — | — | Compound (147) | 1:1:0:0:1 |
| Y4 | Compound (7) | — | Compound (75) | Compound (86) | — | 2:0:1:1:0 |
| Y5 | Compound (9) | — | Compound (76) | — | — | 1:0:1:0:0 |
| Y6 | Compound (11) | — | Compound (77) | — | — | 1:0:1:0:0 |
| Y7 | Compound (14) | — | — | — | Compound (147) | 1:0:0:0:1 |
| Y8 | Compound (16) | Compound (62) | — | — | Compound (146) | 1:1:0:0:1 |
| Y9 | Compound (19) | Compound (63) | — | — | Compound (148) | 1:1:0:0:1 |
| Y10 | Compound (20) | Compound (71) | — | — | — | 1:1:0:0:0 |
| Y11 | Compound (22) | — | — | — | Compound (146) | 1:0:0:0:1 |
| Y12 | Mixture (1:1) of Compound (31) and Compound (20) | — | — | Compound (85) | — | 1:0:0:1:0 |
| Y13 | — | — | — | Compound (86) | Compound (146) | 0:0:0:3:1 |
| Y14 | — | — | Compound (76) | — | Compound (148) | 0:0:1:0:1 |
| Y15 | Compound (13) | — | — | — | Compound (146) | 1:0:0:0:1 |
| Y16 | Compound (15) | — | — | — | Compound (146) | 1:0:0:0:1 |

Production Examples 17 to 28

Thermal transfer recording sheets (M1) to (M12) were obtained in the same manner as in Production Example 1, except using compounds of the "compounding ratio" of General Formulae (2) and (6) to (9) shown in Table 2 in place of using the compound (1) in Production Example 1.

Examples 2 to 14, Comparative Example 1 to 4

Image sample (2) to (14) and comparative image samples (1) to (4) were produced by the same operation as that of Example 1, except changing the combination of the thermal transfer recording sheets Y1, M1, and C1 to the combination of the thermal transfer recording sheets shown in Table 4.

TABLE 2

| Thermal transfer recording sheet | General Formula (2) | General Formula (6) | General Formula (7) | General Formula (8) | General Formula (9) | Compounding ratio |
|---|---|---|---|---|---|---|
| M1 | Compound (44) | — | — | — | — | 1:0:0:0:0 |
| M2 | Compound (32) | Compound (89) | Compound (99) | — | — | 2:1:1:0:0 |
| M3 | Compound (34) | — | — | Compound (107) | — | 3:0:0:1:0 |
| M4 | Compound (37) | Compound (91) | — | Compound (105) | Compound (118) | 2:2:0:1:1 |
| M5 | Compound (52) | Compound (92) | Compound (102) | — | — | 3:1:1:0:0 |
| M6 | Compound (54) | Compound (90) | Compound (98) | Compound (109) | — | 2:1:1:1:0 |
| M7 | Compound (42) | Compound (93) | Compound (100) | Compound (107) | Compound (115) | 4:1:1:1:1 |
| M8 | Compound (52) | — | — | — | Compound (116) | 2:0:0:0:1 |
| M9 | Compound (54) | — | — | Compound (108) | Compound (117) | 3:0:0:1:1 |
| M10 | Compound (44) | Compound (94) | Compound (101) | — | Compound (114) | 2:1:1:0:1 |
| M11 | — | — | — | Compound (108) | Compound (116) | 0:0:0:1:1 |
| M12 | — | Compound (92) | Compound (98) | — | — | 0:2:1:0:0 |

Production Examples 29 to 35

Thermal transfer recording sheets (C1) to (C7) were obtained in the same manner as in Production Example 1, except using compounds of the "compounding ratio" of General Formulae (10) to (12) shown in Table 3 in place of using the compound (1) in Production Example 1.

TABLE 3

| Thermal transfer recording sheet | General Formula (10) | General Formula (11) | General Formula (12) | Compounding ratio |
|---|---|---|---|---|
| C1 | Compound (124) | Compound (133) | Compound (136) | 1:1:1 |
| C2 | Compound (125) | Compound (132) | Compound (137) | 1:2:1 |
| C3 | Compound (124) | — | Compound (136) | 1:0:1 |
| C4 | Compound (125) | Compound (132) | — | 1:1:0 |
| C5 | Compound (123) | Compound (131) | — | 1:1:0 |
| C6 | Compound (124) | Compound (133) | Compound (141) | 2:1:1 |
| C7 | Compound (123) | Compound (132) | — | 2:1:0 |

Example 1

Image samples were prepared by transferring, onto a photographic paper, the thermal transfer recording sheets Y1, M1, and C1 using a modified machine of a printer, Selphy, manufactured by CANON KABUSHIKI KAISHA. For the image samples, data obtained by changing and combining the print output of each of Y, M, and C from 0% to 100% in increments of 10% were used.

<Evaluation>

[Evaluation of Color Reproduction Area]

The image samples (1) to (14) and the comparative image samples (1) to (4) obtained by thermal transfer were measured for chromaticity (L*, a*, and b*) in the L*a*b* color system of the combination of a primary color and a secondary color using a reflection densitometer, Spectro Lino (manufactured by Gretag Macbeth AG).

The color reproduction area was simulated using the measurement results, and then the color reproduction area of the first quadrant which was a red reproduction region was evaluated. As the reference, the color reproduction area of Comparative Example 2 not containing the compound of General Formula (1) and the compound of General Formula (2) was set to 100%.

| 115%≤Color reproduction area | A: |
| 105%≤Color reproduction area<115% | B: |
| Color reproduction area<105% | C: |

[Evaluation of Print Density]

In the image samples obtained by thermal transfer, a 100% print portion of each of magenta, yellow, and cyan was measured for the spectrum reflection density using a reflection densitometer, Spectro Lino (manufactured by Gretag Macbeth AG).

The print density was specified as a value obtained by adding the spectrum reflection density of each of magenta, yellow, and cyan. The image samples having a print density of 6.0 or more were evaluated to be excellent.

| 6.2≤Print density | A: |
| 6.0≤Print density<6.2 | B: |
| Print density<6.0 | C: |

[Evaluation of Reproducibility of Process Black]

In the image samples obtained by thermal transfer, the process black portion was measured for the spectrum reflection spectrum using a reflection densitometer, Spectro Lino (manufactured by Gretag Macbeth AG).

The reproducibility of the process black was specified as a difference (ΔE) between the maximum reflectivity and the minimum reflectivity of the measured spectrum reflection spectra. Then, the case where ΔE was smaller than 0.02 was judged that the reproducibility of the process black was good.

| ΔE<0.01 | A: |
| 0.01≤ΔE<0.02 | B: |
| 0.0≤ΔE | C: |

The evaluation results above are shown in Table 4.

TABLE 4

| | Y sheet | M sheet | C sheet | Color gamut area | Print density | Process black |
|---|---|---|---|---|---|---|
| Example 1 | Y1 | M1 | C1 | B (105) | A (6.22) | B (0.011) |
| Example 2 | Y2 | M2 | C2 | A (117) | A (6.23) | A (0.009) |
| Example 3 | Y3 | M3 | C3 | A (115) | A (6.35) | A (0.008) |
| Example 4 | Y4 | M4 | C4 | B (112) | B (6.00) | A (0.009) |
| Example 5 | Y5 | M5 | C5 | B (110) | B (6.11) | B (0.015) |
| Example 6 | Y6 | M6 | C6 | A (115) | B (6.09) | B (0.013) |
| Example 7 | Y7 | M7 | C7 | A (116) | A (6.42) | A (0.008) |
| Example 8 | Y8 | M8 | C1 | B (108) | B (6.01) | B (0.011) |
| Example 9 | Y9 | M9 | C2 | B (111) | B (6.14) | B (0.011) |
| Example 10 | Y10 | M10 | C3 | A (119) | A (6.53) | A (0.007) |
| Example 11 | Y11 | M3 | C4 | B (107) | B (6.11) | B (0.010) |
| Example 12 | Y12 | M10 | C5 | B (112) | A (6.41) | A (0.007) |
| Example 13 | Y15 | M3 | C4 | B (108) | A (6.39) | B (0.011) |
| Example 14 | Y16 | M3 | C4 | B (110) | A (6.35) | B (0.012) |
| Comparative Example 1 | Y13 | M11 | C4 | C (96) | C (5.98) | B (0.019) |
| Comparative Example 2 | Y13 | M12 | C2 | C (100) | C (5.78) | C (0.024) |
| Comparative Example 3 | Y14 | M4 | C3 | C (105) | C (5.90) | C (0.022) |
| Comparative Example 4 | Y4 | M11 | C2 | C (98) | C (5.81) | B (0.014) |

As shown in Table 4, by the use of the thermal transfer recording sheet having the ink layer containing the compound represented by General Formula (1) and the ink layer containing the compound represented by General Formula (2), an image having more excellent red reproducibility, higher density, and a smaller difference between the maximum reflectivity and the minimum reflectivity, i.e., an image achieving both black representation and red representation, is obtained as compared with the case of using the comparative thermal transfer recording sheet.

<Production of Ink Set>
<Preparation of Dispersion Liquid (1)>

20 parts of β-naphthalene sulfonic acid formaldehyde condensate, 55 parts of ion exchange water, 10 parts of diethylene glycol, and 15 parts of the compound (1) were mixed and dispersed for 3 hours by an Attritor (manufactured by NIPPON COKE & ENGINEERING CO., LTD.) to obtain a dispersion liquid (1).

<Preparation of Dispersion Liquids (2) to (7)>

Dispersion liquids (2) to (7) were obtained by the same preparation method as that of the dispersion liquid (1), except using the corresponding compounds shown in Table 5 for the dispersion liquids in place of using the compound (1).

TABLE 5

| | Compound to be used |
|---|---|
| Dispersion liquid (1) | Compound (1) |
| Dispersion liquid (2) | Compound (71) |
| Dispersion liquid (3) | Compound (74) |
| Dispersion liquid (4) | Compound (44) |
| Dispersion liquid (5) | Compound (89) |
| Dispersion liquid (6) | Compound (132) |
| Dispersion liquid (7) | Compound (124) |

<Preparation of Ink A>

10 parts of the dispersion liquid (1), 10 parts of the dispersion liquid (2), 10 parts of glycerol, 10 parts of diethylene glycol, and 40 parts of ion exchange water were mixed, and then the pH of the mixture was adjusted to be 8 by sodium hydroxide, and then the mixture was stirred for 2 hours. The resultant mixture was filtered through a Fluoro Porefilter FP-100 (Trade name, manufactured by Sumitomo Denko Co., Ltd.) to obtain an ink A.

<Preparation of Inks B to G>

Inks B to G were obtained by the same preparation method as that of the ink A, except changing the dispersion liquid (1) and the dispersion liquid (2) to the dispersion liquids shown in Table 6 in the preparation of the ink A.

The inks A to C are yellow inks, the inks D to F are magenta inks, and the inks F and G are cyan inks.

TABLE 6

| | Dispersion liquid to be used |
|---|---|
| Ink A | Dispersion liquid 1: 10 parts |
| | Dispersion liquid 2: 10 parts |
| Ink B | Dispersion liquid 1: 10 parts |
| | Dispersion liquid 3: 10 parts |
| Ink C | Dispersion liquid 3: 20 parts |
| Ink D | Dispersion liquid 4: 10 parts |
| | Dispersion liquid 5: 10 parts |
| Ink E | Dispersion liquid 5: 20 parts |
| Ink F | Dispersion liquid 6: 10 parts |
| | Dispersion liquid 7: 10 parts |
| Ink G | Dispersion liquid 7: 20 parts |

Preparation of Dyed Substance

Example 15

The ink A, the ink D, and the ink F described above were placed in a LaboJet-500 (Trade name, manufactured by MICROJET), the print output of each of the Y, the M, and the C was changed in increments of 10% from 0% to 100%, and then an image was formed on an ink jet sublimation transfer paper of a basis weight 70 g/square meter (manufactured by Sanryu Co., Ltd.) using the combined data. Next, the surface to which the inks were given was laminated on polyester satin (manufactured by Toray Industries, Inc.) in such a manner as to face each other, and then the laminate was heated at 200° C. for 45 seconds with a heat pressing machine to obtain a dyed substance (1).

Example 16

A dyed substance (2) was obtained in the same manner as in Example 15, except changing the ink A to the ink B in Example 15.

Comparative Example 5

A dyed substance (3) was obtained in the same manner as in Example 15, except changing the ink A to the ink C, the ink D to the ink E, and the ink F to the ink G in Example 15.
<Evaluation>
[Evaluation of Color Reproduction Area]

The dyed substances (1) to (3) were measured for chromaticity ($L^*$, $a^*$, and $b^*$) in the $L^*a^*b^*$ color system of the combination of a primary color and a secondary color using a reflection densitometer, Spectro Lino (manufactured by Gretag Macbeth AG).

The color reproduction area was simulated using the measurement results, and then the color reproduction area of the first quadrant which was a red reproduction region was evaluated. As the reference, the color reproduction area of Comparative Example 5 not containing the compound of General Formula (1) and the compound of General Formula (2) was set to 100%.

| | |
|---|---|
| 115%≤Color reproduction area | A: |
| 105%≤Color reproduction area<115% | B: |
| Color reproduction area<105% | C: |

[Evaluation of Print Density]

In the dyed substances (1) to (3), a 100% print portion of each of magenta, yellow, and cyan was measured for the spectrum reflection density using a reflection densitometer, Spectro Lino. The print density was specified as a value obtained by adding the spectrum reflection density of each of magenta, yellow, and cyan.

| | |
|---|---|
| 4.5≤Print density | A: |
| 4.2≤Print density<4.5 | B: |
| Print density<4.2 | C: |

[Evaluation of Reproducibility of Process Black]

In the dyed substance (1) to (3), the process black portion was measured for the spectrum reflection spectrum using a reflection densitometer, Spectro Lino.

The reproducibility of the process black was specified as a difference (ΔE) between the maximum reflectivity and the minimum reflectivity of the measured spectrum reflection spectra. Then, the case where ΔE was smaller than 0.02 was judged that the reproducibility of the process black was good.

| | |
|---|---|
| $\Delta E<0.01$ | A: |
| $0.01 \leq \Delta E<0.02$ | B: |
| $0.02 \leq \Delta E$ | C: |

The evaluation results above are shown in Table 7.

TABLE 7

| | Y ink | M ink | C ink | Color gamut area | Print density | Process black |
|---|---|---|---|---|---|---|
| Example 15 | Ink A | Ink D | Ink F | A (120) | A (4.6) | A (0.008) |
| Example 16 | Ink B | Ink D | Ink F | A (117) | A (4.7) | A (0.009) |
| Comparative Example 5 | Ink C | Ink E | Ink G | C (100) | C (4.1) | C (0.025) |

As shown in Table 7, by the use of the ink set at least containing the ink containing the compound represented by General Formula (1) and the ink containing the compound represented by General Formula (2), an image having more excellent red reproducibility, higher density, and a smaller difference between the maximum reflectivity and the minimum reflectivity, i.e., an image achieving both black representation and red representation, is obtained as compared with the case of using the comparative ink set.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2015-085300, filed Apr. 17, 2015, which is hereby incorporated by reference herein in its entirety.

What is claimed is:

1. An ink set separately comprising:
   a first ink containing a compound represented by General Formula (1) shown below; and
   a second ink containing a compound represented by General Formula (2) shown below, General Formula (1)

wherein, in General Formula (1),
$R_1$ represents an alkyl group, an unsubstituted aryl group, an aryl group having a substituent, an acyl group, a carboxy group, an alkoxycarbonyl group, a carboxamide group, an amino group, an alkoxy group, or a cyano group,
$R_2$ represents an alkyl group, an unsubstituted aryl group, or an aryl group having a substituent,
$R_3$ represents an alkyl group, an unsubstituted aryl group, an aryl group having a substituent, or a heterocyclic group,
$R_4$ and $R_5$ each independently represent an alkyl group, and
when $R_1$ to $R_3$ are the aryl groups having a substituent, the substituent is an alkyl group, an alkoxy group, or a sulfonic acid salt group, General Formula (2)

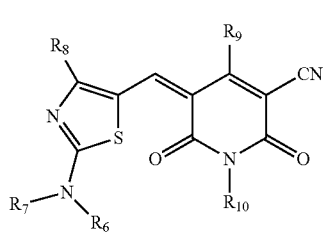

wherein, in General Formula (2), $R_6$ and $R_7$ each independently represent an alkyl group, $R_8$ represents a hydrogen atom, an alkyl group, an unsubstituted aryl group, or an aryl group having a substituent, $R_9$ represents an alkyl group, an unsubstituted aryl group, or an aryl group having a substituent, $R_{10}$ represents a hydrogen atom, an alkyl group, an unsubstituted aryl group, an aryl group having a substituent, or $-N(-R_{11})R_{12}$, wherein $R_{11}$ and $R_{12}$ each independently represent a hydrogen atom, an alkyl group, or an acyl group and $R_{11}$ and $R_{12}$ may be bonded to form a ring, and when $R_8$ to $R_{10}$ are the aryl groups having a substituent, the substituent is an alkyl group or an alkoxy group.

2. The ink set according to claim 1, wherein $R_1$ in General Formula (1) above is an alkyl group, an aryl group, an acyl group, or a carboxy group.

3. The ink set according to claim 1, wherein at least either the first ink or the second ink further contains a compound selected from the group consisting of compounds represented by General Formulae (3) to (13) shown below, General Formula (3)

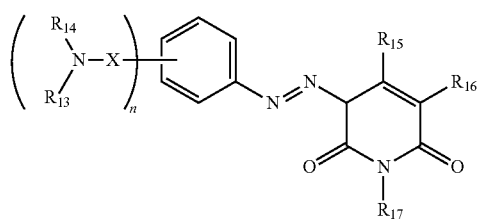

wherein, in General Formula (3), either $R_{13}$ or $R_{14}$ represents an alkyl group and the other one represents a hydrogen atom or an alkyl group, $R_{15}$ represents an alkyl group, an unsubstituted aryl group, an aryl group having a substituent, or an amino group, $R_{16}$ represents a hydrogen atom, a cyano group, a carbamoyl group, an alkoxycarbonyl group, or a carboxamide group, $R_{17}$ represents a hydrogen atom, an alkyl group, an unsubstituted aryl group, an aryl group having a substituent, or $-N(-R_{18})R_{19}$, wherein and $R_{18}$ and $R_{19}$ each independently represent a hydrogen atom, an alkyl group, or an acyl group and $R_{18}$ and $R_{19}$ may be bonded to each other to form a ring, when $R_{15}$ and $R_{17}$ are the aryl groups having a substituent, the substituent is an alkyl group, X represents a carbonyl group or a sulfonyl group, and n represents an integer of 1 to 3, General Formula (4)

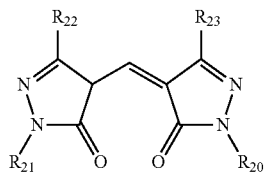

wherein, in General Formula (4), $R_{20}$ to $R_{23}$ each independently represent an alkyl group, an unsubstituted aryl group, or an aryl group having a substituent, and when $R_{20}$ to $R_{23}$ are the aryl groups having a substituent, the substituent is an alkyl group or an alkoxy group, General Formula (5)

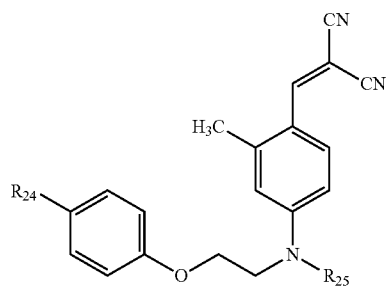

wherein, in General Formula (5), $R_{24}$ and $R_{25}$ each independently represent an alkyl group, an unsubstituted aryl group, or an aryl group having a substituent, and when $R_{24}$ and $R_{25}$ are the aryl groups having a substituent, the substituent is an alkyl group, General Formula (6)

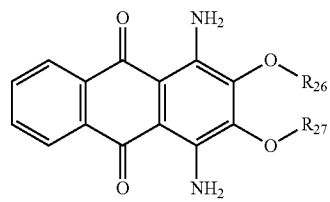

wherein, in General Formula (6), $R_{26}$ and $R_{27}$ each independently represent an alkyl group, an unsubstituted aryl group, or an aryl group having a substituent, and when $R_{26}$ and $R_{27}$ are the aryl groups having a substituent, the substituent is an alkoxy group, General Formula (7)

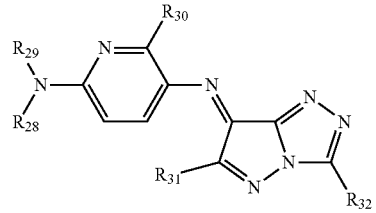

wherein, in General Formula (7), $R_{28}$ to $R_{32}$ each independently represent an alkyl group, an unsubstituted aryl group, or an aryl group having a substituent, and when $R_{28}$ to $R_{32}$ are the aryl groups having a substituent, the substituent is an alkyl group or an alkoxy group, General Formula (8)

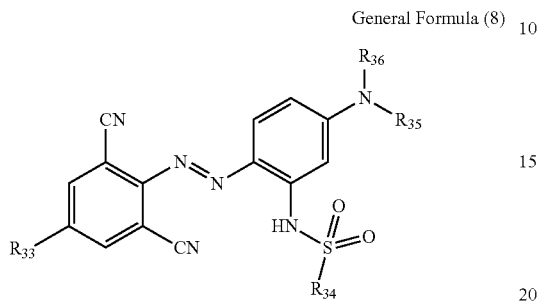

wherein, in General Formula (8), $R_{33}$ to $R_{36}$ each independently represent an alkyl group, an unsubstituted aryl group, or an aryl group having a substituent, and when $R_{33}$ to $R_{36}$ are the aryl groups having a substituent, the substituent is an alkyl group, General Formula (9)

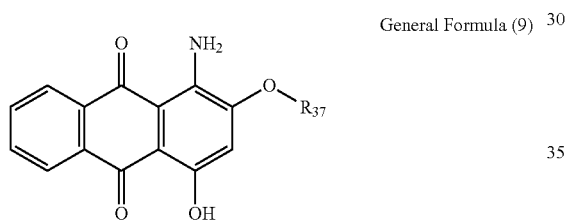

wherein, in General Formula (9), $R_{37}$ represents an alkyl group, an unsubstituted aryl group, an aryl group having a substituent, or —($R_{52}$—O)n-$R_{53}$, wherein $R_{52}$ is an alkylene, $R_{53}$ is an alkyl group, and n is 1 or 2, and, when $R_{37}$ is the aryl group having a substituent, the substituent is an alkyl group or an alkoxy group, General Formula (10)

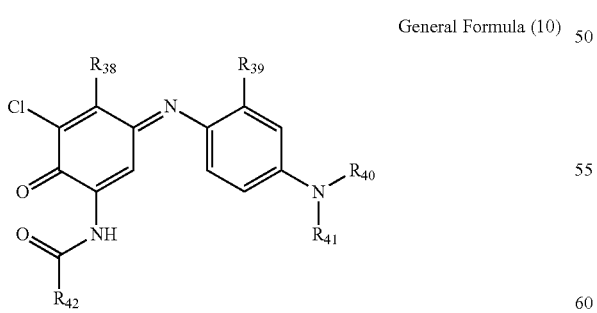

wherein, in General Formula (10), $R_{38}$ to $R_{42}$ each independently represent an alkyl group, an unsubstituted aryl group, or an aryl group having a substituent, and when $R_{38}$ to $R_{42}$ are the aryl groups having a substituent, the substituent is an alkyl group, General Formula (11)

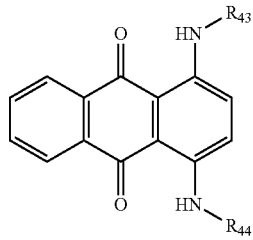

wherein, in General Formula (11), $R_{43}$ and $R_{44}$ each independently represent an alkyl group, an unsubstituted aryl group, or an aryl group having a substituent, and when $R_{43}$ and $R_{44}$ are the aryl groups having a substituent, the substituent is an alkyl group, General Formula (12)

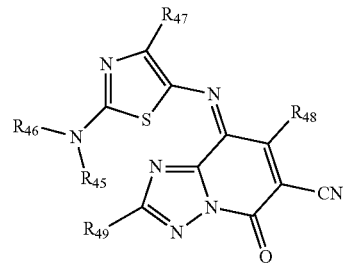

wherein, in General Formula (12), $R_{45}$ to $R_{49}$ each independently represent an alkyl group, an unsubstituted aryl group, or an aryl group having a substituent, and when $R_{45}$ to $R_{49}$ are the aryl groups having a substituent, the substituent is an alkyl group, General Formula (13)

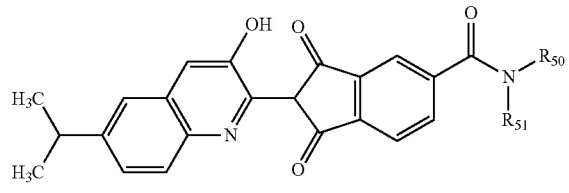

wherein, in General Formula (13), $R_{50}$ and $R_{51}$ each independently represent an alkyl group, an unsubstituted aryl group, or an aryl group having a substituent, and when $R_{50}$ and $R_{51}$ are the aryl groups having a substituent, the substituent is an alkyl group.

4. A thermal transfer recording sheet, comprising:
a first ink layer containing a compound represented by General Formula (1) shown below; and
a second ink layer containing a compound represented by General Formula (2), General Formula (1)

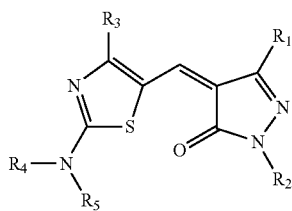

wherein, in General Formula (1), $R_1$ represents an alkyl group, an unsubstituted aryl group, an aryl group having a substituent, an acyl group, a carboxy group, an alkoxycarbonyl group, a carboxamide group, an amino group, an alkoxy group, or a cyano group, $R_2$ represents an alkyl group, an unsubstituted aryl group, or an aryl group having a substituent, $R_3$ represents an alkyl group, an unsubstituted aryl group, an aryl group having a substituent, or a heterocyclic group, $R_4$ and $R_5$ each independently represent an alkyl group, and when $R_1$ to $R_3$ are the aryl groups having a substituent, the substituent is an alkyl group, an alkoxy group, or a sulfonic acid salt group, General Formula (2)

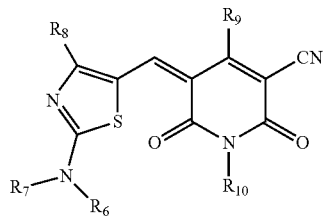

wherein, in General Formula (2), $R_6$ and $R_7$ each independently represent an alkyl group, $R_8$ represents a hydrogen atom, an alkyl group, an unsubstituted aryl group, or an aryl group having a substituent, $R_9$ represents an alkyl group, an unsubstituted aryl group, or an aryl group having a substituent, $R_{10}$ represents a hydrogen atom, an alkyl group, an unsubstituted aryl group, an aryl group having a substituent, or —N(—$R_{11}$)$R_{12}$, wherein $R_{11}$ and $R_{12}$ each independently represent a hydrogen atom, an alkyl group, or an acyl group and $R_{11}$ and $R_{12}$ may be bonded to form a ring, and when $R_8$ to $R_{10}$ are the aryl groups having a substituent, the substituent is an alkyl group or an alkoxy group.

5. The thermal transfer recording sheet according to claim 4, wherein $R_1$ in General Formula (1) above is an alkyl group, an aryl group, an acyl group, or a carboxy group.

6. The thermal transfer recording sheet according to claim 4, wherein at least either the first ink layer or the second ink layer further contains a compound selected from the group consisting of compounds represented by General Formulae (3) to (13) shown below, General Formula (3)

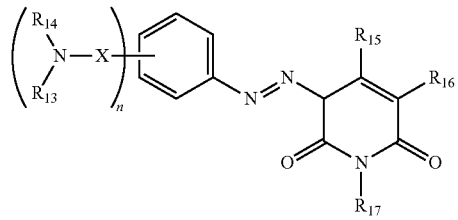

wherein, in General Formula (3), either $R_{13}$ or $R_{14}$ represents an alkyl group and the other one represents a hydrogen atom or an alkyl group, $R_{15}$ represents an alkyl group, an unsubstituted aryl group, an aryl group having a substituent, or an amino group, $R_{16}$ represents a hydrogen atom, a cyano group, a carbamoyl group, an alkoxycarbonyl group, or a carboxamide group, $R_{17}$ represents a hydrogen atom, an alkyl group, an unsubstituted aryl group, an aryl group having a substituent, or —N(—$R_{18}$)$R_{19}$, wherein $R_{18}$ and $R_{19}$ each independently represent a hydrogen atom, an alkyl group, or an acyl group and $R_{18}$ and $R_{19}$ may be bonded to each other to form a ring, when $R_{15}$ and $R_{17}$ are the aryl groups having a substituent, the substituent is an alkyl group, X represents a carbonyl group or a sulfonyl group, and n represents an integer of 1 to 3, General Formula (4)

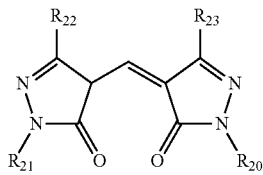

wherein, in General Formula (4), $R_{20}$ to $R_{23}$ each independently represent an alkyl group, an unsubstituted aryl group, or an aryl group having a substituent, and when $R_{20}$ to $R_{23}$ are the aryl groups having a substituent, the substituent is an alkyl group or an alkoxy group, General Formula (5)

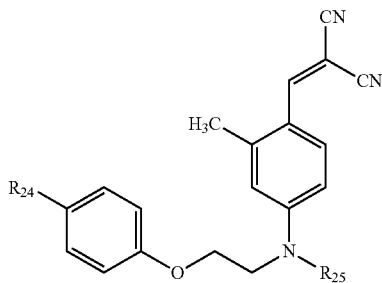

wherein, in General Formula (5), $R_{24}$ and $R_{25}$ each independently represent an alkyl group, an unsubstituted aryl group, or an aryl group having a substituent, and when $R_{24}$ and $R_{25}$ are the aryl groups having a substituent, the substituent is an alkoxy group, General Formula (6)

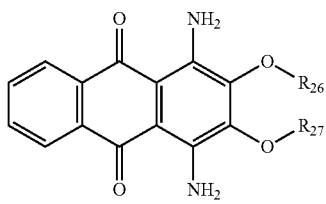

wherein, in General Formula (6), $R_{26}$ and $R_{27}$ each independently represent an alkyl group, an unsubstituted aryl group, or an aryl group having a substituent, and when $R_{26}$ and $R_{27}$ are the aryl groups having a substituent, the substituent is an alkyl group, General Formula (7)

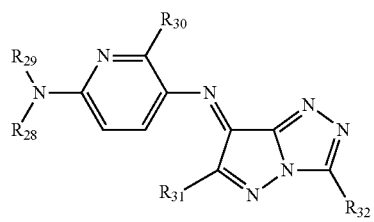

wherein, in General Formula (7), $R_{28}$ to $R_{32}$ each independently represent an alkyl group, an unsubstituted aryl group, or an aryl group having a substituent, and when $R_{28}$ to $R_{32}$ are the aryl groups having a substituent, the substituent is an alkyl group or an alkoxy group, General Formula (8)

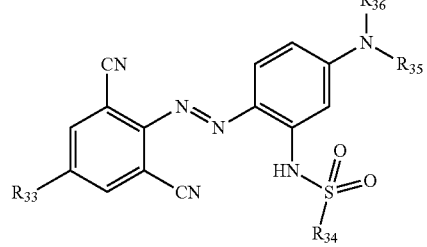

wherein, in General Formula (8), $R_{33}$ to $R_{36}$ each independently represent an alkyl group, an unsubstituted aryl group, or an aryl group having a substituent, and when $R_{33}$ to $R_{36}$ are the aryl groups having a substituent, the substituent is an alkyl group, General Formula (9)

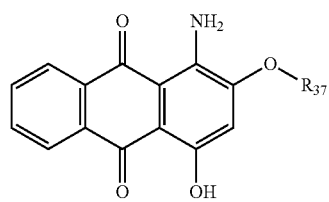

wherein, in General Formula (9), $R_{37}$ represents an alkyl group, an unsubstituted aryl group, an aryl group having a substituent, or —($R_{52}$—O)n-$R_{53}$, wherein $R_{52}$ is an alkylene, $R_{53}$ is an alkyl group, and n is 1 or 2, and, when $R_{37}$ is the aryl group having a substituent, the substituent is an alkyl group or an alkoxy group, General Formula (10)

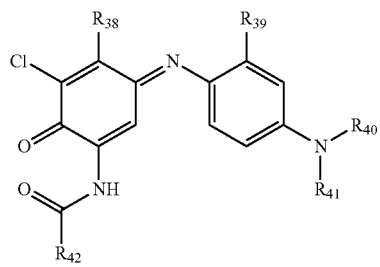

wherein, in General Formula (10), $R_{38}$ to $R_{42}$ each independently represent an alkyl group, an unsubstituted aryl group, or an aryl group having a substituent, and when $R_{38}$ to $R_{42}$ are the aryl groups having a substituent, the substituent is an alkyl group, General Formula (11)

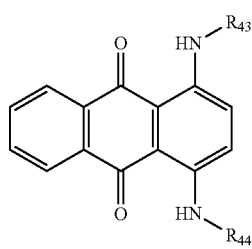

wherein, in General Formula (11), $R_{43}$ and $R_{44}$ each independently represent an alkyl group, an unsubstituted aryl group, or an aryl group having a substituent, and when $R_{43}$ and $R_{44}$ are the aryl groups having a substituent, the substituent is an alkyl group, General Formula (12)

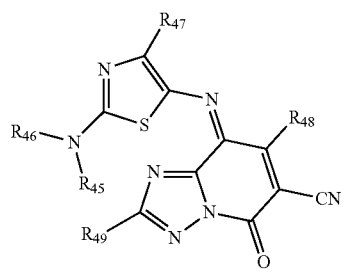

wherein, in General Formula (12), $R_{45}$ to $R_{49}$ each independently represent an alkyl group, an unsubstituted aryl group, or an aryl group having a substituent, and when $R_{45}$ to $R_{49}$ are the aryl groups having a substituent, the substituent is an alkyl group, General Formula (13)
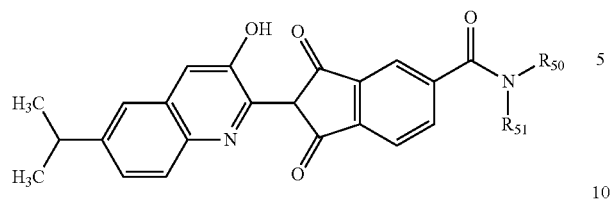
wherein, in General Formula (13), $R_{50}$ and $R_{51}$ each independently represent an alkyl group, an unsubstituted aryl group, or an aryl group having a substituent, and when $R_{50}$ and $R_{51}$ are the aryl groups having a substituent, the substituent is an alkyl group.
* * * * *